(12) United States Patent
Okawa et al.

(10) Patent No.: US 8,147,854 B2
(45) Date of Patent: Apr. 3, 2012

(54) COSMETICS COMPRISING A MODIFIED ORGANOPOLYSILOXANE

(75) Inventors: Tadashi Okawa, Ichihara (JP); Tomohiro Iimura, Sodegaura (JP)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 606 days.

(21) Appl. No.: 11/993,436

(22) PCT Filed: Jun. 21, 2006

(86) PCT No.: PCT/JP2006/312848
§ 371 (c)(1),
(2), (4) Date: May 6, 2009

(87) PCT Pub. No.: WO2006/137576
PCT Pub. Date: Dec. 28, 2006

(65) Prior Publication Data
US 2010/0028391 A1 Feb. 4, 2010

(30) Foreign Application Priority Data

Jun. 21, 2005 (JP) ................................ 2005-180066
Jun. 21, 2005 (JP) ................................ 2005-180072
Jun. 16, 2006 (JP) ................................ 2006-166880

(51) Int. Cl.
C08G 77/22 (2006.01)
(52) U.S. Cl. ..................... 424/401; 528/26; 424/70.122; 424/70.12; 424/59; 556/419
(58) Field of Classification Search .................. 528/26; 424/70.122, 70.12, 401; 556/419
See application file for complete search history.

(56) References Cited

U.S. PATENT DOCUMENTS

| 5,194,251 | A | 3/1993 | Halloran et al. |
| 5,976,557 | A * | 11/1999 | Friedrich et al. ............. 424/401 |
| 6,110,230 | A | 8/2000 | Friedrich et al. |
| 6,696,053 | B1 * | 2/2004 | Ma et al. ................... 424/70.27 |

FOREIGN PATENT DOCUMENTS

| EP | 0095676 A2 | 12/1983 |
| EP | 0842656 A2 | 5/1998 |
| EP | WO 2006137576 A1 | 12/2006 |
| JP | 02243612 A2 | 9/1990 |
| JP | 07215817 A | 8/1995 |
| JP | 08012524 A | 1/1996 |
| JP | 08012545 A | 1/1996 |
| JP | 08012546 A | 1/1996 |
| JP | 08109263 A | 4/1996 |
| JP | 09241511 A | 9/1997 |
| JP | 10158150 A | 6/1998 |
| JP | 10036219 A | 10/1998 |
| JP | 11193331 A | 7/1999 |
| JP | 2000063225 A | 2/2000 |
| JP | 2000281523 A | 10/2000 |
| JP | 2003226611 A | 8/2003 |
| WO | WO 2005063856 A | 7/2005 |
| WO | WO 2006137577 A2 | 12/2006 |

OTHER PUBLICATIONS

PCT International Search Report for PCT/JP2006/312849, Dec. 21, 2006, 3 pages.
English language abstract for EP0842656, extracted from espacenet.com, Sep. 23, 2008.
English language abstract for JP 02243612, extracted from PAJ database, Sep. 30, 2008.
English language translation and abstract for JP07215817, extracted from searching PAJ, Sep. 23, 2008, 42 pages.
English language translation and abstract for JP08012524, extracted from searching PAJ, Sep. 30, 2008, 33 pages.
English language translation and abstract for JP08012545, extracted from searching PAJ, Sep. 30, 2008, 30 pages.
English language translation and abstract for JP08012546, extracted from searching PAJ, Sep. 30, 2008, 32 pages.
English language translation and abstract for JP08109263, extracted from searching PAJ, Sep. 30, 2008, 68 pages.
English language translation and abstract for JP09241511, extracted from searching PAJ, Sep. 30, 2008, 37 pages.
English language translation and abstract for JP10036219, extracted from searching PAJ, Sep. 30, 2008, 43 pages.
English language translation and abstract for JP10158150, extracted from searching PAJ, Sep. 23, 2008, 51 pages.
English language translation and abstract for JP11193331, extracted from searching PAJ, Sep. 30, 2008, 59 pages.
English language translation and abstract for JP2000063225, extracted from searching PAJ, Sep. 30, 2008, 75 pages.
English language translation and abstract for JP2000281523, extracted from searching PAJ, Oct. 3, 2008, 109 pages.
English language translation and abstract for JP2003226611, extracted from searching PAJ, Sep. 30, 2008, 81 pages.
English language abstract for WO2005063856, extracted from espacenet.com, Sep. 23, 2008.
PCT International Search Report PCT/JP2006/312848, dated Oct. 23, 2006, 4 pages.

* cited by examiner

*Primary Examiner* — Margaret Moore
(74) *Attorney, Agent, or Firm* — Howard & Howard Attorneys PLLC

(57) ABSTRACT

This invention relates to a cosmetics characterized in that it contains a gelling agent comprising an organopolysiloxane having a silicon-bonded organic group represented by general formula: $R^1$—X—CO—NH—[X—N(—CO—X—$R^1$)]$_p$—X— (1) (wherein $R^1$ designates a group containing metal salt of a carboxylic acid represented by formula —COO$^-$($M^{n+}$)$_{1/n}$ (where M is a metal that has a valence of 1 or higher); X's designate the same or different $C_2$ to $C_{14}$ bivalent hydrocarbon groups; and p designates an integer from 0 to 10.). Preferably, the organosiloxane has an optionally substituted $C_9$ or more univalent hydrocarbon group. Adding the gelling agent makes it possible to provide a cosmetic possessing superior temporal stability, water retention properties, sensory feel, gloss, curl retention, and cleansing power.

21 Claims, 2 Drawing Sheets

[Figure 1.]
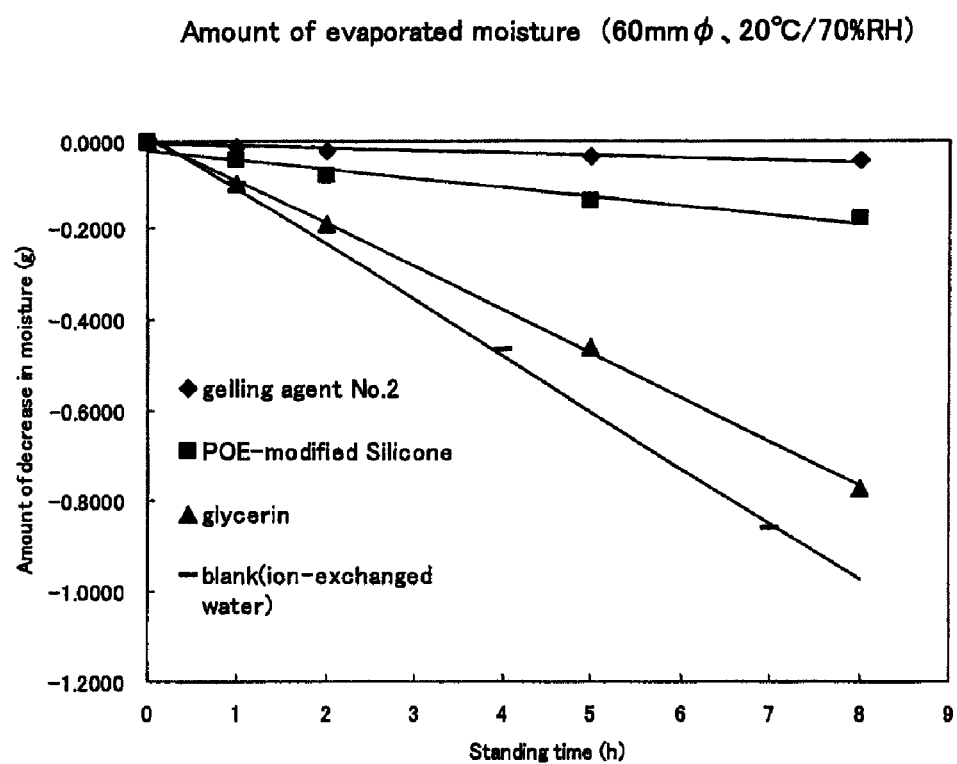

[Figure 2.]
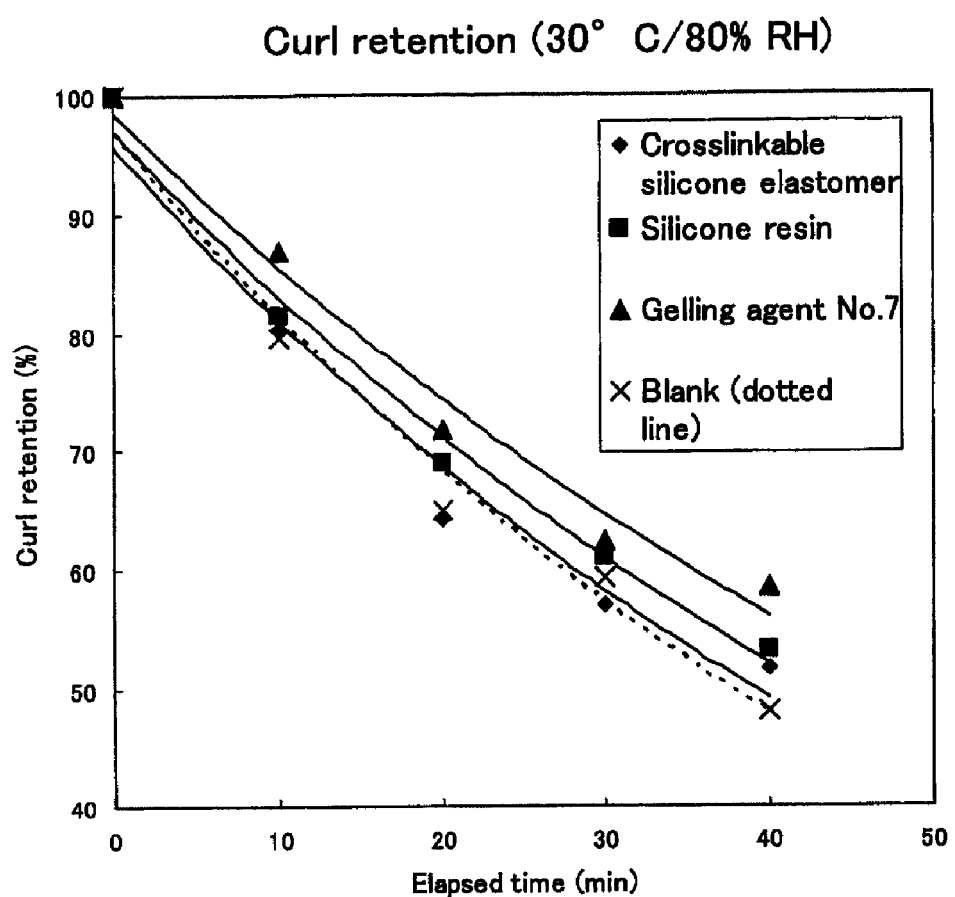

COSMETICS COMPRISING A MODIFIED ORGANOPOLYSILOXANE

RELATED APPLICATIONS

This application claims priority to and all the advantages of International Patent Application No. PCT/JP2006/312848, filed on Jun. 21, 2006, which claims priority to Japanese Patent Application No. JP2005-180066, filed on Jun. 21, 2005, Japanese Patent Application No. JP2005-180072, filed on Jun. 21, 2005, and Japanese Patent Application No. JP2006-166880, filed on Jun. 16, 2006.

FIELD OF THE INVENTION

The present invention is related to a cosmetic and a cosmetic product obtained by containing a gelling agent of a silicone oil, a low-polarity organic compound, and a non-polar organic compound, as well as to a gelatinous composition comprising said gelling agent and a compound selected from the group consisting of a silicone oil, a no-polar organic compound, or a low-polar organic compound, or mixtures thereof. More specifically, it relates to a cosmetic and a cosmetic product obtained by adding the gelling agent or the gel composition having superior properties in temporal stability, sensory feel, detergent properties, moisture retention, gloss, makeup durability, curl retention, sagging prevention properties, and external appearance of the product, its cleansing power, etc.

BACKGROUND OF THE INVENTION

Gelling agents capable of gelling various types of organic liquids are known as alkali-metal salts or alkali-earth-metal salts of higher fatty acids, 1,2-hydroxy stearic acids, dibenzylidene sorbitols, amino acid derivatives, amide or urea compounds, etc. However, these known gelling agents are poorly compatible with silicone oils and therefore are unsuitable for gelling silicones. Moreover, the use of such gelling agents is limited only to those applications where they can provide stable gelling of both silicone oils and fats.

Due to such properties as excellent spread-ability, ability of imparting a refreshed feel, lubricity, hydrophilic property, stability, etc., silicone oils (in particular low-viscosity silicone oils) find wide applications, especially in cosmetic products. However, silicone oils are usually poorly compatible with other oils, and therefore cannot provide stability of products that contain such combinations. For example, it is impossible to provide stability in situations where wax is added for obtaining a gel product based on low-viscosity silicone oils. Another problem associated with such products is a turbid appearance. Replacement of waxes with a cross-linked silicone imparts to the product a feel of stickiness and eliminates the original feel of freshness inherent in silicone oils. Japanese Laid-Open Patent Application Publication (Kokai) H7-215817 discloses t discloses a silicone-oil gelling agent in the form of a polyether-graft type organopolysiloxane, but the gelling agent requires the simultaneous addition of an appropriate amount of water, and the obtained composition is not stable with time and is not completely satisfactory with regard to feel in use.

Japanese Laid-Open Patent Application Publication (Kokai) H10-158150 discloses the use of carboxamide polysiloxanes in cosmetic preparations, as well as in skin-care and hair-care compositions as aqueous emulsions of carboxamide polysiloxanes. However, the aforementioned publication does not teach that the organopolysiloxanes that contain carboxyamide groups can be used as gelling agents for silicone oils, non-polar organic compounds, or low-polarity organic compounds. Japanese Laid-Open Patent Application Publication (Kokai) H08-109263 describes the use of organo(poly)siloxane modified with polyvalent metal carboxylate as a gelling agent of silicone oils and shows the use of this agent in cosmetic products. Nevertheless, the gel composition having sufficient viscous property and a modulus of elasticity cannot be obtained without using this gelling agent in large quantities.

PCT publication WO2005/063856 discloses gelling agents as an organopolysiloxane having a silicon-bonded organic group containing amino alcohol salt of a carboxylic acid. However, these gelling agents and gelatinous composition prepared with those gelling agents have poor resistance to heat. E.g., when the gelling agents or cosmetics containing these gelling agents are stood at higher temperature than 100° C. for several hours in the manufacturing process, the desired gelling properties may be lacked after cooling for the intramolecular dehydration reaction under high temperature. In addition, the aforementioned PCT publication discloses only methylpolysiloxane having a silicon-bonded organic group containing amino alcohol salt of a carboxylic acid. Such organically-modified methylpolysiloxane have poor solubility in organic oils containing many alkyl groups. For this, such gelling agents do not have sufficient and general-purpose property to obtain stable gelatinous composition comprising many kinds of organic oils. These placed limitations on the method of manufacture and on compounding uses especially in the field of cosmetics.

SUMMARY OF THE INVENTION

The present invention provides a cosmetics containing a gelling agent suitable for gelling silicone oils, low-polarity liquid organic compounds and/or non-polar liquid organic compounds without the use of water, as well as a cosmetics containing the gelatinous composition characterized by excellent thermal stability, temporal stability, readily able to be combined with cosmetics and having thixotropic rheologic properties. The present invention also provides a cosmetic and a cosmetic product obtained by adding the gelling agent or the gelatinous composition having superior properties in temporal stability, moisture retention, sensory feel, gloss, curl retention, detergent properties, sagging prevention properties, and external appearance of the product, its cleansing power, etc.

The inventors herein have found that the aforementioned objects can be achieved by a cosmetic or a cosmetic product containing a gelling agent comprising an organopolysiloxane having a silicon-bonded organic group represented by general formula (1):

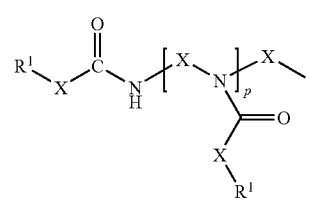

(1)

wherein $R^1$ designates a group containing metal salt of a carboxylic acid represented by formula —COO$^-$ (M$^{n+}$)$_{1/n}$ (where M is a metal that has a valence of 1 or higher, and n is the valence of M); X's designate the same or different $C_2$–$C_{14}$ bivalent hydrocarbon groups; and p designates an integer from 0 to 10, and by using a gelatinous composition that consists of 1 to 99 wt. % of a gelling agent (A) and 99 to 1 wt. % of a compound selected from the group consisting of a silicone oil, a non-polar organic compound, or a low-polarity organic compound (B).

Furthermore, the inventors have found that the aforementioned objects can be more preferably achieved by using a cosmetic or a cosmetic product containing a gelling agent comprising an organopolysiloxane having a silicon-bonded organic group represented by general formula (1) and an optionally substituted $C_9$ or more univalent hydrocarbon group.

The aforementioned gelling agent of the present invention possesses high gelling capacity and can be used for gelling silicone oils, in particular, hydrophobic silicone oils and non-polar liquid organic compounds, without the use of water. Especially, the aforementioned gelling agent of the organopolysiloxane having an optionally substituted $C_9$ or more univalent hydrocarbon group possesses excellent gelling capacity to a non-polar organic compound or a low-polarity organic compound having many alkyl groups for its solubility in these organic compounds. The present invention provides a cosmetic containing a gelling agent which, when combined with silicone oils, non-polar organic compounds and low-polarity organic compounds, is capable of forming a gel composition that possesses thixotropic rheologic properties and is readily combined with cosmetics without the use of water. This invention also provides a cosmetic and a cosmetic product obtained by adding the gelling agent or the gel composition having superior properties in temporal stability, moisture retention, sensory feel, gloss, curl retention, detergent properties, sagging prevention properties, external appearance of the product, etc.

BRIEF DESCRIPTION OF THE DRAWINGS

FIG. 1 is the moisture retention properties of the gelling agent No. 2 etc. obtained in Reference Example 4.

FIG. 2 is the hair-curl retention properties of the gelling agent No. 7 etc. obtained in Reference Example 5.

DETAILED DESCRIPTION OF THE INVENTION

The cosmetic and cosmetic product of the present invention are characterized by containing a gelling agent (ingredient (a)) comprising an organopolysiloxane having a silicon-bonded organic group (—Y) represented by general formula (1):

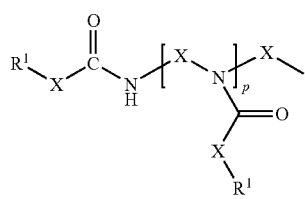
(1)

wherein $R^1$ designates a group containing metal salt of a carboxylic acid represented by formula —COO⁻ $(M^{n+})_{1/n}$ (where M is a metal that has a valence of 1 or higher, and n is the valence of M); X's designate the same or different bivalent hydrocarbon groups having $C_2$ to $C_{14}$; and p designates an integer from 0 to 10. The organic groups of general formula (1) can be exemplified by specific groups of the following formulae, where M designates a metal that has a valence of 1 or higher, and n is the valence of M:

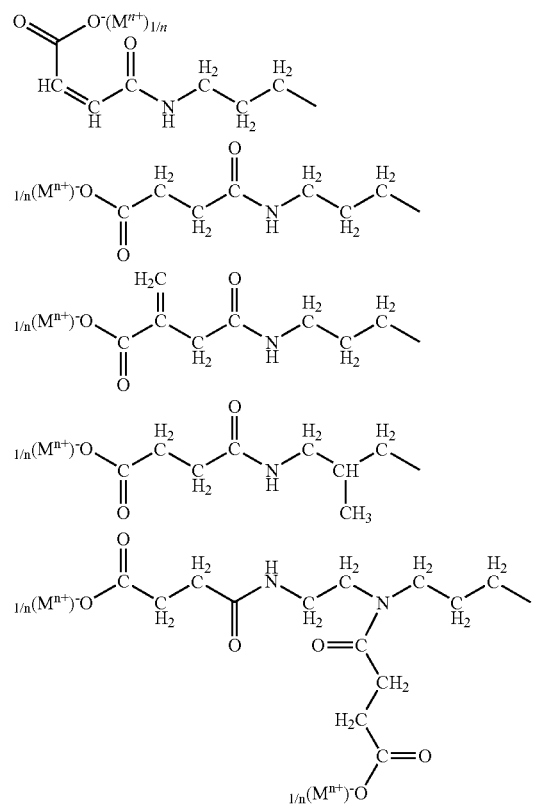

The organopolysiloxane having a silicon-bonded organic group of general formula (1) contains at least one of the siloxane units represented by the following formula (4) or (5):

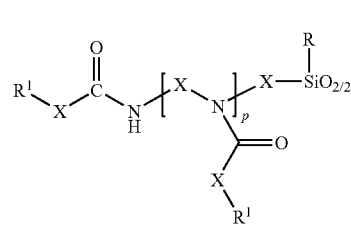
(4)

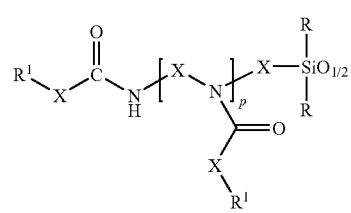
(5)

In these formulae, R designates an optionally substituted $C_1$ to $C_8$ univalent hydrocarbon group (except for the organic group represented by general formula (1)); $R^1$, X and p are the same as defined as above.

Furthermore, the cosmetic and cosmetic product of the present invention are characterized by preferably containing a gelling agent (ingredient (a)) comprising an organopolysiloxane having an aforementioned silicon-bonded organic group (—Y) represented by general formula (1) and a silicon-bonded optionally substituted $C_9$ or more univalent hydrocarbon group (—Z). Containing such "long-chain" univalent hydrocarbon group and aforementioned organic group represented by general formula (1) within a molecule makes it possible to increase the solubility of the organopolysiloxane to a non-polar organic compound or a low-polarity organic compound having many alkyl groups.

Such silicon-bonded optionally substituted $C_9$ or more univalent hydrocarbon group (—Z) may be same or identical to each other. This univalent hydrocarbon group (—Z) may have a linear-chain, or a branched molecular structure. Having a linear-chain structure is preferable. The non-substituted univalent hydrocarbon groups can be exemplified by $C_9$ or more, preferably $C_9$ to $C_{1000}$ alkyl groups, aryl groups or aralkyl groups. The substituted univalent hydrocarbon groups can be exemplified by $C_9$ or more, preferably $C_9$ to $C_{1000}$ perfluoroalkyl groups, aminoalkyl groups, amidoalkyl groups {except for the organic groups represented by general formula (1)} or carbinol groups. Most preferable univalent hydrocarbon group (—Z) is $C_{10}$ to $C_{45}$ alkyl groups represented by the formula: —$(CH_2)_v$—$CH_3$ (v is an integer in the range of 9 to 44).

The organopolysiloxane having a silicon-bonded organic group of general formula (1) (—Y) and silicon-bonded an optionally substituted $C_9$ or more univalent hydrocarbon group (—Z) contains at least one of the aforementioned siloxane units represented by the following formula (4) or (5) and at least one of the siloxane units represented by the following formula (6) or (7):

In these formulae, —R designates an optionally substituted $C_1$ to $C_8$ univalent hydrocarbon group {except for the organic group represented by general formula (1)}, —Z designates an aforementioned optionally substituted $C_9$ or more univalent hydrocarbon group {except for the organic group represented by general formula (1)}.

The gelling agent of the present invention may also consist of the following four types of siloxane units: $R_3SiO_{1/2}$, $R_2SiO_{2/2}$, $RSiO_{3/2}$, and $SiO_{4/2}$, where the R designate optionally substituted $C_1$ to $C_8$ univalent hydrocarbon groups. The non-substituted univalent hydrocarbon groups can be represented by methyl, ethyl, propyl, or similar alkyl groups; phenyl, tolyl, xylyl, or similar aryl groups; or aralkyl groups. The substituted univalent hydrocarbon groups can be represented by 3,3,3-trifluoropropyl, 3,3,4,4,4-pentafluyorobutyl, or similar perfluoroalkyl groups; 3-aminopropyl, 3-(aminoethyl)aminopropyl, or similar aminoalkyl groups; acetylaminoalkyl, or similar amidoalkyl groups {except for the organic groups represented by general formula (1)}. A part of R may be substituted with an alkoxy group. The alkoxy group may be exemplified by a methoxy, ethoxy, or a propoxy group. Typically R is an alkyl groups of $C_1$ to $C_6$, in particular, methyl group.

The organopolysiloxane that has a silicon-bonded organic group of general formula (1) may contain in one molecule at least one siloxane unit of formula (4) or (5). However, from the point of view of better gelling properties, it is preferable to have two or more such units. For the same purpose as above, it is preferable that the siloxane units of formula (4) or (5) be used in an amount of 0.1 to 50 mole %, more preferably 0.5 to 30 mole % of all soloxane units.

Furthermore, the organopolysiloxane having a silicon-bonded organic group of general formula (1) (—Y) and silicon-bonded an optionally substituted $C_9$ or more univalent hydrocarbon group (—Z) may contain in one molecule at least one siloxane unit of formula (4) or (5), and at least one siloxane units of formula (6) or (7). However, from the point of view of better solubility of the organopolysiloxane to organic compounds having many alkyl groups, it is preferable to have two or more such siloxane units of formula (6) or (7). For the same purpose as above, it is preferable that the siloxane units of formula (6) or (7) is used in an amount of 0.1 to 75 mole %, more preferably 5 to 30 mole % of all siloxane units.

The organopolysiloxane that has a silicon-bonded organic group of general formula (1) may contain at least one organic group of formula (1) within one molecule. However, from the point of view of better gelling properties, it is preferable to have two or more such groups in an amount of more than 0.5 wt. %, and preferably more than 1.0 wt. %. The aforementioned organopolysiloxane may have a linear, branched, or cyclic molecular structure, of which the linear molecular structure is preferable. There are no restrictions with regard to the bonding position of the organic group of formula (1). When the aforementioned organopolysiloxane has a linear or a branched molecular structure, the organic group of formula (1) can be bonded to molecular terminals or to the sides of the molecular chains on the organopolysiloxane. Bonding to the sides of the molecular chains on the organopolysiloxane is preferable.

Furthermore, from the point of view of better gelling properties and solubility to organic compounds having many alkyl groups, it is preferable to have at least one, more preferably two or more silicon-bonded optionally substituted $C_9$ or more univalent hydrocarbon groups (—Z) in the aforementioned organopolysiloxane. When the aforementioned organopolysiloxane has a linear or a branched molecular structure, the optionally substituted $C_9$ or more univalent hydrocarbon groups (—Z) can be bonded to molecular terminals or to the sides of the molecular chains on the organopolysiloxane. Bonding to the sides of the molecular chains on the organopolysiloxane is preferable.

A representative linear organopolysiloxane having a silicon-bonded organic group (—Y) of formula (1) is represented by the following general formula (2);

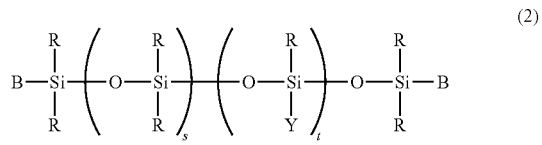

Wherein R designates the same as defined above, Y designates an organic group of general formula (1), and B is R or Y. When t=0, at least one of the two B's is Y. Above "s" designates an integer in the range of 10 to 100,000, preferable in the range of 100 to 10,000; "t" designates an integer between 0 and 50, preferably 1 to 30. It is recommended that t/(s+t) is in the range of 0.001 to 0.05, preferably 0.001 to 0.03. At room temperature, the organopolysiloxane having a silicon-bonded organic group of general formula (1) may comprise a viscous liquid having a turbidity from microscopic to white, or it may comprise a paste-like or a solid substance. The paste-like or solid state at room temperature is preferable.

In similar manner, a representative linear organopolysiloxane having a silicon-bonded organic group of general formula (1) (—Y) and a silicon-bonded optionally substituted $C_9$ or more univalent hydrocarbon group (—Z) is represented by the following general formula (3).

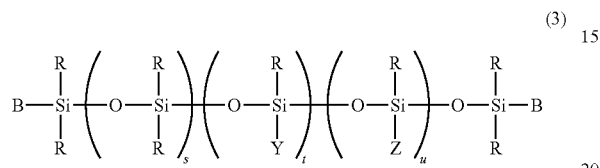

(3)

Wherein R is the same as defined above, Y is an organic group of general formula (1), and B is R, Y or Z. When t=0, at least one of the two B's is Y. When u=0, at least one of the two B's is Z. When t=0 and u=0, one of the two B's is Y and another is Z. Above "s" designates an integer in the range of 10 to 100,000, preferable in the range of 100 to 10,000; "t" designates an integer between 0 and 50, preferably 1 to 30, and "u" designates an integer between 0 and 1000, preferably 5 to 200. It is recommended that t/(s+t+u) is in the range of 0.001 to 0.05, preferably 0.001 to 0.03 and that u/(s+t+u) is in the range of 0.01 to 0.75, preferably 0.05 to 0.30. Furthermore, It is recommended that (s+t+u) is in the range of 20 to 5,000 from the point of view of better gelling properties and handling property as a raw material. At room temperature, the organopolysiloxane having a silicon-bonded organic group of general formula (1) (—Y) and a silicon-bonded optionally substituted $C_9$ or more univalent hydrocarbon group (—Z) may comprise a viscous liquid having a turbidity from microscopic to white, or it may comprise a paste-like or a solid substance. The paste-like or solid state at room temperature is preferable.

The organopolysiloxane having a silicon-bonded organic group of formula (1) can be prepared, e.g., by reacting an organopolysiloxane having a silicon-bonded organic group of general formula (8) and a metal compound of formula (9) given as below:

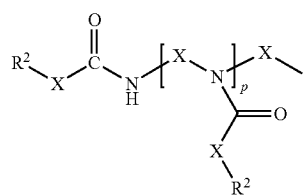

(8)

(where $R^2$ is a carboxylic group represented by formula —COOH or an ester carboxylate group represented by formula —COOR$^4$; $R^4$ is a univalent hydrocarbon group having C1 to C10; X's designate the same or different bivalent hydrocarbon groups having $C_2$ to $C_{14}$; and p designates an integer from 0 to 10.);

$(M^{n+})_j(L^{j-})_n$ (9)

(where M is a metal that has a valence of 1 or higher; L is an oxygen atom or an anion; n is the valence of M; and j is the valence of L).

The organopolysiloxane having the organic group of aforementioned general formula (8) can be typically prepared by reacting an amine functional organopolysiloxane with a cyclic carboxylic acid anhydride. The aforementioned amino-functional organopolysiloxane can be exemplified by an organopolysiloxane having an amino group bonded to silicon via a bifunctional hydrocarbon group, and an organopolysiloxane having a silicon-bonded organic group of general formula (10):

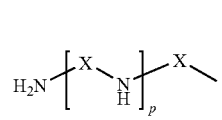

(10)

(where X's designate the same or different bivalent hydrocarbon groups having $C_2$ to $C_{14}$; and p designates an integer from 0 to 10. Normally, the bivalent hydrocarbon group X is an alkylene group, preferably a $C_2$ to $C_6$ alkylene group, and, more preferably, an ethylene group or a propylene group)

Cyclic carboxylic acid anhydrides useful to prepare the carboxyamide organopolysiloxane are illustrated by the following representative list; succinic acid anhydride, maleic acid anhydride, itaconic acid anhydride, citraconic acid anhydride, allylsuccinic acid anhydride, phthalic acid anhydride, norbornane-dicarboxylic acid anhydride, cyclohexane-dicarboxylic acid anhydride, nonenylsuccinic acid anhydride, and decenylsuccinic acid anhydride. Among these, the succinic acid anhydride is most preferable as it provides high gelling capacity and high transparency in gelatinous compositions. The reaction between amine groups contained in organopolysiloxanes and cyclic carboxylic acid anhydrides are known. In the presence of non-solvents or appropriate solvents, such reactions precede exothermically. A mole ratio between the first-mentioned amine groups and the second-mentioned carboxylic acid anhydride can be arbitrarily chosen, but if the amount of residual amine groups is too high, the gel-like product becomes tacky, and the gelling capacity is reduced. Typically, a ratio of the carboxylic acid anhydride to amine groups on the organopolysiloxane range from 0.5 to 1, preferably from 0.9 to 1.

Organic groups represented by formula (8), that can be prepared as above-described method, can be exemplified by compounds of the following formulae:

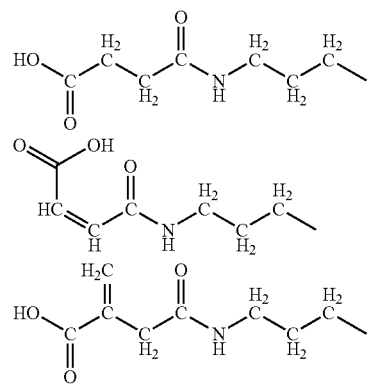

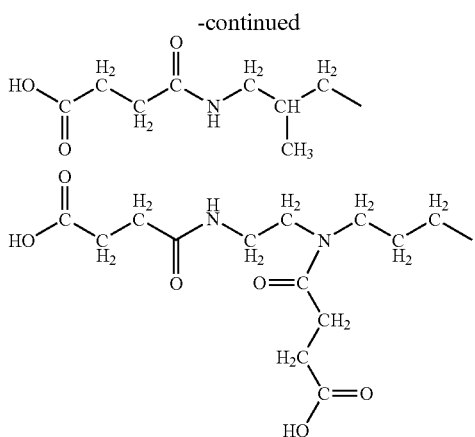

The terminal carboxyl or ester carboxylate group of an organic group represented by formula (8) can be converted into an organic group of formula (1) that comprises a metal salt of a carboxylic acid represented by formula —COO$^-$ (M$^{n+}$)$_{1/n}$ (where M is a metal having a valence of 1 or higher, and n is the valence of M) by reacting a metal compound of aforementioned general formula (9): (M$^{n+}$)$_j$(L$^{j-}$)$_n$. Wherein M is a metal that has a valence of 1 or higher; L is an oxygen atom or an anion; n is the valence of M; and j is the valence of L. Metals represented by M may be exemplified by lithium, sodium, potassium, magnesium, calcium, barium, iron, cobalt, aluminum, nickel, copper, vanadium, molybdenum, niobium, zinc, tantalum, etc. Preferably, the metals represented by M are alkali metals such as sodium and potassium, alkali earth metals such as magnesium and calcium, and aluminum in view of transparency and stability of gelatinous compositions regarding this invention. Sodium and potassium are most suitable for using univalent alkali metals makes it possible to change flowability of the obtained gelatinous composition reversibly at the change of the temperature. In contrast, the organopolysiloxanes having organic groups with amino alcohol salts as gelling agents have poor resistance to heat. For this, when the gelling agents or cosmetics containing the gelling agents are stood at a temperature higher than 110° C. for several hours in the manufacturing process, the desired gelling properties may be lacked after cooling for the dehydration reaction under high temperature.

The following are specific examples of appropriate metal compounds: lithium hydroxide, sodium hydroxide, potassium hydroxide, magnesium hydroxide, calcium hydroxide, aluminum hydroxide, iron hydroxide, copper hydroxide, zinc hydroxide, or a similar metal hydroxide; methoxy lithium, methoxy sodium, methoxy potassium, ethoxy lithium, ethoxy sodium, ethoxy potassium, t-butoxy potassium. or a similar metal alcoholate; phenoxy lithium, phenoxy sodium, phenoxy potassium, paramethoxyphenoxy sodium, or a similar alkali metal arylate; lithium, sodium, potassium, or a similar alkali metal; lithium hydride, sodium hydride, potassium hydride, or a similar alkali metal hydride; methyl lithium, n-butyl lithium, sec-butyl lithium, t-butyl lithium, n-butyl sodium, n-butyl potassium, diethyl zinc, or a similar alkylmetal compound; phenyl lithium, phenyl sodium, potassium naphthalenide, or a similar optionally substituted aryl alkali metal; copper fluoride, potassium chloride, aluminum chloride, magnesium chloride, zinc chloride, iron chloride, copper chloride, titanium tetrachloride, calcium bromide, aluminum bromide, magnesium bromide, zinc bromide, iron bromide, or a similar metal halide; magnesium oxide, copper oxide, titanium oxide, zinc oxide, or a similar metal oxide; calcium carbonate, barium carbonate, copper carbonate, or similar metal carbonate; magnesium sulfate, potassium sulfate, zinc sulfate, iron sulfate, copper sulfate, aluminum sulfate, or a similar metal sulfate. Most preferable of the above metal compounds from the point of view of reactivity, cost, and workability are metal hydroxides, metal alcholates, and metal halides.

Reaction may also be carried out between metal compounds of formula (9) and an organopolysiloxane modified directly with carboxylic acid or with a carboxylic acid ester, but after formation of metal salts, reactions may occur between various metal compounds. Reaction conditions between metal compounds of general formula (9) and univalent and/or polyvalent metal salts of carboxylic acid, ester carboxylate, or carboxylic acid cannot be unequivocally prescribed for all cases since they depend on the type of the metal compound that participates in the reaction, but taking into account reactivity of the metal compounds, it is recommended to conduct the reaction by dispersing the metal compounds in appropriate media.

Normally, the reaction of forming an organic group of formula (1) that contains a carboxylic acid metal salt represented by formula —COO$^-$ (M$^{n+}$)$_{1/n}$ (where M is a metal of a valence equal to 1 or higher, and n is the valence of M) easily proceeds at a temperature in the range from room temperature to about 100° C. Although the reaction mole ratio between the carboxylic groups or ester carboxylate groups of organopolysiloxane that contains organic groups of formula (8) and the metal compounds of formula (9) may be arbitrary, it is recommended to have the aforementioned mole ratio in the range of 0.1 to 5.0, preferably 0.4 to 2.0. If the mole ratio of the reaction exceeds the upper recommended limit, the organopolysiloxane that has an organic group of formula (1) will not be able to demonstrate sufficient gelling properties. If, on the other hand, the aforementioned mole ratio is below the recommended lower limit, the reaction system will become strongly alkaline, especially in the case of a reaction with a basic metal compound, and this may break siloxane bonds of the organopolysiloxane and decrease stability of the obtained gel.

Only a part of a terminal carboxylic group or a terminal ester carboxylate of an organic group of general formula (8) can be neutralized by the metal compound of formula (9) (M$^{n+}$)$_j$(L$^{j-}$)$_n$ and converted into an organic group of general formula (1). The same method can be used for adjusting softness of the resulting gel. For example, an organopolysiloxane having an organic group of formula (8) and an organic group of formula (1) can be prepared by adding a metal compound of formula (9) (M$^{n+}$)$_j$(L$^{j-}$)$_n$, which amount is 80% neutral relative to the terminal carboxylic group or the terminal ester carboxylate of an organic group of general formula (8). A gel obtained with the use of the last-mentioned organopolysiloxane is softer by touch than a gel obtained with the use of an organopolysiloxane having an organic group of formula (1) prepared by adding a metal salt of formula (9) (M$^{n+}$)$_j$(L$^{j-}$)$_n$, which amount is 100% neutral to the terminal carboxylic group or the terminal ester carboxylate of an organic group of general formula (8).

In similar manner, the organopolysiloxane having a silicon-bonded organic group (—Y) of general formula (1) and a silicon-bonded optionally substituted C$_9$ or more univalent hydrocarbon group (—Z) can be prepared by reacting an organopolysiloxane having a silicon-bonded organic group of general formula (8) and a silicon-bonded optionally substituted C$_9$ or more univalent hydrocarbon group (—Z) with a metal compound of formula (9). Then, the organopolysiloxane having a silicon-bonded organic group of general formula (8) and a silicon-bonded optionally substituted $C_9$ or more univalent hydrocarbon group (—Z) with a metal compound of formula (9) can be typically prepared by reacting an amine functional organopolysiloxane having a silicon-bonded optionally substituted $C_9$ or more univalent hydrocarbon group (—Z) with a cyclic carboxylic acid anhydride as above.

The aforementioned amine functional organopolysiloxane having a silicon-bonded optionally substituted $C_9$ or more univalent hydrocarbon group (—Z) can be prepared by some known synthesis reaction. For example, such organopolysiloxane can be prepared by the hydrosilylation reaction between organohydrogenpolysiloxane, a compound having optionally substituted $C_9$ or more univalent hydrocarbon group and unsaturated hydrocarbon group within a molecule, and an amino-functional compound having unsaturated hydrocarbon group within a molecule.

Since the aforementioned organopolysiloxane having a silicon-bonded organic group (—Y) of general formula (1) has an excellent gelling properties by mixing it with a silicone oil, a non-polar organic compound, or a low-polarity organic compound under heating conditions with subsequent cooling to room temperature, it is suitable for use as a gelling agent for these compounds. Especially, the aforementioned organopolysiloxane having a silicon-bonded organic group (—Y) of general formula (1) and a silicon-bonded optionally substituted $C_9$ or more univalent hydrocarbon group (—Z) has an excellent gelling capacity to a non-polar organic compound or a low-polarity organic compound having many alkyl groups for its solubility in these organic compounds.

Since these organopolysiloxane gelling agent has low gelling capacity with regard to methanol, ethanol, or similar polar organic compounds, such solvents can be used in the preparation of the organopolysiloxane gelling agent. For example, a silicone oil or a non-polar liquid organic compound may be mixed with a polar organic compound, and an organopolysiloxane having an organic group of formula (8) and a metal compound of formula (9) are added to the aforementioned mixture. Then, neutralization reaction between the carboxyl groups of the carboxyamide-containing organopolysiloxane and a metal compound is carried out to produce the reaction product, an organopolysiloxane having an organic group of formula (1), in a liquid mixture. After removal of the aforementioned polar organic compound by distillation under reduced pressure, a gelatinous silicone oil or a gelled non-polar liquid organic compound is obtained.

The cosmetic of the present invention is characterized by containing a gelatinous composition comprised of:
(a) 1 to 99 wt. % of a gelling agent of aforementioned organopolysiloxanes and
(b) 99 to 1 wt. % of a compound selected from the group consisting of a silicone oil, a no-polar organic compound, or a low-polar organic compound, or mixtures thereof.

In the aforementioned gelatinous composition ingredient (a) functions as a gelling agent of ingredient (b). Each of a silicone oil, non-polar, or low-polarity organic compound of ingredient (b) can be used independently, or may be mixed with two or three constituents such as silicone oils, non-polar organic compounds or low-polarity organic compounds. Ingredient (a) and (b) should be mixed in a ratio within the range of (a):(b)=(1 to 99):(99 to 1) wt. %, preferably (2 to 40):(98 to 60) wt. %, and even more preferably (10 to 30):(90 to 70) wt. %.

The silicone oil should be one that is not contained in ingredient (a) and may have a cyclic, linear-chain, or a branched molecular structure. In order to facilitate gelling, the use of a hydrophobic silicone oil is preferable and the oil should have a viscosity in the range of 0.65 to 100,000 mm²/s, preferably in the range of 0.65 to 10,000 mm²/s at 25° C. The following are specific examples of such oils: octamethyl cyclotetrasiloxane, tetramethylcyclopentasiloxane, or a similar cyclic diorganopolysiloxane; hexamethyldisiloxane, dimethylpolysiloxane capped at both molecular terminals with trimethylsiloxy groups, methylphenylpolysiloxane capped at both molecular terminals with trimethylsiloxy groups, methylalkylpolysiloxane capped at both molecular terminals with trimethylsiloxy groups, or a similar linear-chain diorganopolysiloxane, methyl tristrimethylsiloxysilane, ethyl tristrimethylsiloxysilane, propyl tristrimethylsiloxysilane, tetrakis tristrimethylsiloxysilane, or a similar branched organopolysiloxane. Of these, preferable are volatile linear dimethylpolysiloxane, branched methylpolysiloxane and cyclic dimethylpolysiloxane, especially, decamethylcyclopentasiloxane.

More specifically, linear organopolysiloxanes shown by the following general formula (10), cyclic organopolysiloxanes shown by the general formula (11), or branched organopolysiloxanes shown by the general formula (12) are suggested as the silicone oils that constitute a portion or all of ingredient (b).

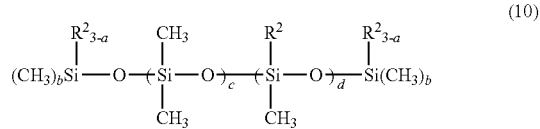

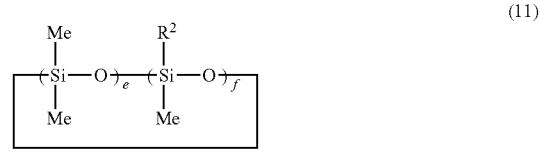

(in general formulae (10) to (12), $R^2$ is a group selected from hydrogen atoms, hydroxyl groups, or $C_{2-30}$ monovalent unsubstituted or fluorine-substituted alkyl groups, aryl groups, amino-substituted alkyl groups, alkoxy groups, and groups represented by $(CH_3)_3SiO\{(CH_3)_2SiO\}_h Si(CH_3)_2CH_2CH_2$. The subscript c is an integer of 0 to 1000, d is an integer of 0 to 1000, c+d is an integer of 1 to 2000, a and b are 0, 1, 2, or 3, e and f are integers of 0 to 8, such that $3 \leq e+f \leq 8$, g is an integer of 1 to 4, and h is an integer of 0 to 500.)

In general formulas (2)~(4), $R^2$ is a group selected from hydrogen atoms, hydroxyl groups, or $C_2$ to $C_{30}$ univalent non-substituted or fluorine-substituted alkyl groups, aryl groups, amino-substituted alkyl groups, alkoxy groups, and groups represented by $(CH_3)_3SiO\{(CH_3)_2SiO\}_h Si(CH_3)_2CH_2CH_2$, which are more specifically exemplified by ethyl, propyl, butyl, pentyl, hexyl, heptyl, octyl, decyl, dodecyl, and other saturated aliphatic hydrocarbon groups; vinyl, allyl, hexenyl, and other unsaturated hydrocarbon groups; cyclopentyl, cyclohexyl, and other saturated alicyclic hydrocarbon groups; phenyl, tolyl, naphthyl, and other aromatic hydrocarbon groups, as well as by groups obtained by partially substituted trimethylsiloxy groups bonded via chain-like polydimethyl siloxane bonds, and/or divalent hydrocarbon groups, or organic groups including mercapto, methacrylic, amino, carboxyl, epoxy groups, and halogen atoms for hydrogen atoms bonded to the carbon atoms of these groups. The subscript c is an integer of 0 to 1000, d is an integer of 0 to 1000, (c+d) is an integer of 1 to 2000, a and b are integers of 0 to 3, e and f are integers of 0 to 8, such that $3 \leq e+f \leq 8$, g is an integer of 1 to 4, and h is an integer of 0 to 500

The cyclic organopolysiloxanes are exemplified by hexamethylcyclotrisiloxane (D3); octamethylcyclotetrasiloxane (D4); decamethylcyclopentasiloxane (D5); dodecamethylcyclohexasiloxane (D6); 1,1-diethylhexamethylcyclotetrasiloxane; phenylheptamethylcyclotetrasiloxane; 1,1-diphenylhexamethylcyclotetrasiloxane; 1,3,5,7-tetravinyltetramethylcyclotetrasiloxane; 1,3,5,7-tetramethylcyclotetrasiloxane; 1,3,5,7-tetracyclohexyltetramethylcyclotetrasiloxane; tris(3,3,3-trifluoropropyl)trimethylcyclotrisiloxane; 1,3,5,7-tetra-(3-aminopropyl)tetramethylcyclotetrasiloxane; 1,3,5,7-tetra-(N-(2-aminoethyl)-3-aminopropyl)tetramethylcyclotetrasiloxane; 1,3,5,7-tetra-(3-mercaptopropyl)tetramethylcyclotetrasiloxane; 1,3,5,7-tetra-(3-glycidoxypropyl)tetramethylcyclotetrasiloxane; 1,3,5,7-tetra-(3-methacryloxypropyl)tetramethylcyclotetrasiloxane; 1,3,5,7-tetra-(3-acryloxypropyl)tetramethylcyclotetrasiloxane; 1,3,5,7-tetra-(3-carboxypropyl)tetramethylcyclotetrasiloxane; 1,3,5,7-tetra-(3-vinyloxypropyl)tetramethylcyclotetrasiloxane; 1,3,5,7-tetra-(p-vinylphenyl)tetramethylcyclotetrasiloxane; 1,3,5,7-tetra-[3-(p-vinylphenyl)propyl]tetramethylcyclotetrasiloxane; 1,3,5,7-tetra-[3-(p-isopropenylbenzoylamino)propyl]tetramethylcyclotetrasiloxane; 1,3,5,7-tetra-(N-methacryloyl-N-methyl-3-aminopropyl)tetramethylcyclotetrasiloxane; 1,3,5,7-tetra-(N-lauroyl-N-methyl-3-aminopropyl)tetramethylcyclotetrasiloxane; 1,3,5,7-tetra-(N-acryloyl-N-methyl-3-aminopropyl)tetramethylcyclotetrasiloxane; 1,3,5,7-tetra-(N,N-bis(methacryloyl)-3-aminopropyl)tetramethylcyclotetrasiloxane; and 1,3,5,7-tetra-(N,N-bis(lauroyl)-3-aminopropyl)tetramethylcyclotetrasiloxane. The linear organopolysiloxanes are exemplified by dimethylpolysiloxane having both ends of the molecular chain blocked by trimethylsiloxy groups, methylphenylpolysiloxane having both ends of the molecular chain blocked by trimethylsiloxy groups, copolymers of methylphenylsiloxane and dimethyl siloxane having both ends of the molecular chain blocked by trimethylsiloxy groups, copolymers of methyl(3,3,3-trifluoropropyl)siloxane and dimethyl siloxane having both ends of the molecular chain blocked by trimethylsiloxy groups, α,ω-dihydroxypolydimethyl siloxane, α,ω-dimethoxypolydimethyl siloxane, tetramethyl-1,3-dihydroxydisiloxane, octamethyl-1,7-dihydroxytetrasiloxane; hexamethyl-1,5-diethoxytrisiloxane, hexamethyldisiloxane, and octamethyltrisiloxane. Cyclic dimethylpolysiloxane is preferable, and decamethylcyclopentasiloxane (D5) is particularly preferable for use as ingredient (b) of the present invention.

It is preferable that the non-polar organic compounds or low-polarity organic compounds are liquid at 5 to 100° C. Compounds suggested as such non-polar organic compounds and low-polarity organic compounds are, for instance, hydrocarbon oils, such as ozokerite, squalane, squalene, ceresin, paraffin, paraffin wax, liquid paraffin, pristane, polyisobutylene, polybutene, micro crystalline wax, Vaseline, etc.; animal and vegetable oils, such as avocado oil, linseed oil, almond oil, Ericerus pela chabannes wax, *perilla* oil, olive oil, cacao butter, Kapok tree wax, kaya oil, carnauba wax; cod-liver oil, candelilla wax, beef tallow, hoof oil, cow bone fat, hardened beef tallow, persic oil, spermaceti wax; hardened oils, wheat germ oil, sesame oil, rice germ oil, rice bran oil, sugarcane wax, camellia Kissi seed oil, safflower oil, shear butter, Paulownia oil, cinnamon oil, jojoba wax, shellac wax, turtle oil, soybean oil, tea seed oil, camellia oil, evening primrose oil, corn oil, lard, rape-seed oil, Japanese tung oil, bran wax, germ oil, horse fat, persic oil, palm oil, palm kernel oil, castor oil, hardened castor oil, castor oil fatty acid methyl ester, sunflower oil, grape seed oil, bayberry wax, jojoba oil, *macadamia* nut oil, yellow beeswax, mink oil, cottonseed oil, cotton wax, Japan wax, sumac kernel oil, montan wax, palm oil, hardened palm oil, cocoglycerides, mutton tallow, peanut oil, lanolin, liquid lanolin, reduced lanolin, lanolin alcohol, hardened lanolin, lanolin acetate, lanolin fatty acid isopropyl ester, lauric acid hexyl ester, POE lanolin alcohol ether, POE lanolin alcohol acetate, lanolin fatty acid polyethylene glycol, POE hydrogenated lanolin alcohol ether, yolk oil, etc.; higher alcohols, such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterols, POE cholesterol ether, monostearyl glycerin ether (batyl alcohol), monooleyl glyceryl ether (selachyl alcohol), etc.; ester oil, such ad diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate; pentaerythritol tetra-2-ethylhexanoate, cetyl octanoate; octyl dodecyl gum ester; oleyl oleate; octyl dodecyl oleate; decyl oleate isononyl isononanoate, neopentyl glycol dicaprate, triethyl citrate, 2-ethylhexyl succinate, amyl acetate; ethyl acetate; butyl acetate; isocetyl stearate, butyl stearate, diisopropyl sebacate; 2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, 2-ethylhexyl myristate; octyl dodecyl myristate, 2-hexyldecyl myristate, myristyl myristate, hexyldecyl dimethyloctanoate, ethyl laurate, hexyl laurate, N-lauroyl L-glutamic acid octyl dodecyl ester, diisostearyl malate, etc.; and glyceride oils, such as acetoglyceride, glyceryl triisooctanoate, glyceryl triisostearate, glyceryl triisopalmitate, glyceryl tri(capryl caprate), glyceryl monostearate, glyceryl di-2-heptylundecanoate, glyceryl trimyristate, diglyceryl myristate isostearate, etc.

Especially, the aforementioned organopolysiloxane having a silicon-bonded organic group (—Y) of general formula (1) and a silicon-bonded optionally substituted $C_9$ or more univalent hydrocarbon group (—Z) has an excellent gelling capacity to a non-polar organic compound or a low-polarity organic compound having many alkyl groups for its solubility in these organic compounds. Such non-polar organic compounds or low-polarity organic compounds having many alkyl groups can be exemplified by the following: paraffin wax, vaseline, n-paraffin, hydrogenated polyisobutylene, ozokerite, ceresin, squalane, pristine, or similar hydrocarbons; avocado oil, almond oil, olive oil, sesame oil, sasanqua oil, safflower oil, soybean oil, Camellia oil, corn oil, rapeseed oil, persic oil, castor oil, cottonseed oil, peanut oil, cacao oil, palm oil, palm kernel oil, Japan wax, coconut oil, or similar vegetable oils or fats; mink oil, egg yolk oil, beef tallow, and pork fat, hardened oil, or similar animal oils or fats; beeswax, carnauba wax, whale wax, lanolin, liquid lanolin, regenerated lanolin, hardened lanolin, candelilla wax, jojoba wax, microcrystalline wax, or a similar wax; palmityl alcohol, stearyl alcohol, oleyl alcohol, lanolin alcohol, cholesterol, phytosterol, 2-hexyldecanol, isostearyl alcohol, 2-octyldecanol, or a similar higher alcohol; methyl formate, ethyl formate, ethyl acetate, propyl acetate, butyl acetate, cetyl octate, isopropyl myristate, isopropyl palmitate, butyl stearate, hexyl laureate, myristyl myristate, olelyl oleate, decyl oleate, octyldecyl myristate, hexyldecyl dimethyloctanate, cetyl lactate, myristyl lactate, diethyl phthalate, dibutyl phthalate, lanolin acetate, ethylene glycol monostearate, propylene glycol monostearate, propylene glycol dioleate, glycerin monostearate, glycerin monooleate, glycerin tri-2-ethylenehexanate, or a similar ester oil; triglyceride of a liquid fatty acid, and artificial skin (mixture of squalane with liquid fatty acid triglyceride, and oleic acid). As ingredient (b) of this invention, these organic compounds may be combined with aforementioned silicone oil in a ratio within the range of (1 to 99):(99 to 1) wt. %.

A gelatinous composition comprising ingredients (a) and (b) can be obtained with excellent transparency by selecting appropriate organic groups of formula (1) that are contained in ingredient (a), especially by selecting types and amounts of univalent or polyvalent metal ion species, as well as types of silicon-bonded hydrocarbon radicals of ingredient (a) and types of ingredient (b). More specifically, the transparent gelatinous composition of an attractive appearance can be obtained by selecting types of bivalent hydrocarbon groups (—X—), values of the subscript "p" and/or types of metal ion $M^{n+}$ in the organic groups represented by formula (1) of component (A) and by selecting component (B) as a colorless, transparent, turbidity-free compound. To obtain a gelatinous composition of a transparent appearance, it is recommended that X is selected as an alkylene group, "p" as 0 or 1, metal ions $M^{n+}$ as sodium ions ($Na^+$), potassium ions ($K^+$), magnesium ion ($Mg^{2+}$), calcium ion ($Ca^{2+}$), or similar alkali metal ions, or similar alkali earth metal ions in the organic groups represented by formula (1); and that component (B) be comprised of dimethylpolysiloxane or methylpolysiloxane having a viscosity of 0.65 to 10,000 $mm^2/s$ at 25° C. The transparent gelatinous composition of this invention is recommended to have a refractive index in the range of 1.20 to 1.60, preferably 1.25 to 1.45.

The aforementioned gelling agent as well as the gelatinous composition composed of ingredient (a) and ingredient (b) can be added to the cosmetics of the present invention to modify its sensory properties to provide abundant smooth and rich sensory feel during application as well as keep the stability of volatile silicone oils such as cyclic organopolysiloxanes, which have a low degree of polymerization and tend to separate easily from the entire body, thereby improving the temporal stability of the cosmetics.

In the cosmetic of the present invention, it is preferable to combine volatile silicones with the gelling agent of the present invention. Volatile silicones is generally useful in skin-refreshing effects, as well as in the ability to firmly bond coating films to the skin in products containing resin ingredients, such as sunscreen, liquid foundation, etc. On the other hand, volatile silicones tend to gradually separate when the cosmetic stored in containers, and, in particular, when cosmetics containing volatile silicones are packed in tube containers, the volatile silicones accumulate at the distal end of the tube and when the tube is used for the first time, initially only separated volatile silicones come out of the tube. The cosmetic of the present invention has an important advantage in permitting suppression of such volatile silicone separation and provide more stable formulations by using volatile silicones in combination with the gelling agent of the present invention, for the gelling agent has superior compatibility with volatile silicones. The amounts, in which the gelling agent of the present composition and the volatile silicones are combined, are preferably 0.1~20 mass % for the gelling agent and 5~80 mass % for the volatile silicones relative to the mass of the cosmetic. When the amounts are in these ranges, the gelling agent of the present invention effectively blends with the volatile silicones and can act to enhance stability. It should be noted that (i) volatile low molecular weight linear or cyclic methyl siloxanes, (ii) volatile or non-volatile, low molecular weight linear or cyclic alkyl or aryl siloxanes, or (iii) low molecular weight linear or cyclic functional siloxanes are suggested as the volatile silicones, with the volatile silicones having average units represented by the formula $(CH_3)_aSiO_{(4-a)/2}$ (the subscript <<a>> has an average value of 2 to 3). The compounds comprise siloxane units joined by ≡Si—O—Si≡ bonds. Representative units are monofunctional "M" units $(CH_3)_3SiO_{1/2}$ and difunctional "D" units $(CH_3)_2SiO_{2/2}$. Here, the presence of trifunctional "T" units $CH_3SiO_{3/2}$ results in the formation of volatile branched linear or cyclic methyl siloxanes. The presence of tetrafunctional "Q" units $SiO_{4/2}$ results in the formation of volatile branched linear or cyclic methyl siloxanes.

The linear volatile silicones are represented by the formula $(CH_3)_3SiO\{(CH_3)_2SiO\}_ySi(CH_3)_3$. The value of the subscript y is in the range of 0 to 5. The cyclic volatile silicones are represented by the formula $\{(CH_3)_2SiO\}_z$, where the value of the subscript z is 3 to 8, and, preferably, 3 to 6. In general, these volatile methyl siloxanes have a boiling point less than 250° C. and a viscosity of 0.65 to 5.0 centistokes ($mm^2/s$). Some representative examples of the volatile linear methyl siloxanes (I) include hexamethyldisiloxane (MM) with a boiling point of 100° C. and a viscosity of 0.65 $mm^2/s$ represented by the formula $(CH_3)_3SiOSi(CH_3)_3$; octamethyltrisiloxane (MDM) with a boiling point of 152° C. and a viscosity of 1.04 $mm^2/s$ represented by the formula $(CH_3)_3SiO(CH_3)_2SiOSi(CH_3)_3$; decamethyltetrasiloxane ($MD_2M$) with a boiling point of 194° C. and a viscosity of 1.53 $mm^2/s$ represented by the formula $(CH_3)_3SiO((CH_3)_2SiO)_2Si(CH_3)_3$; dodecamethylpentasiloxane ($MD_3M$) with a boiling point of 229° C. and a viscosity of 2.06 $mm^2/s$ represented by the formula $(CH_3)_3SiO((CH_3)_2SiO)_3Si(CH_3)_3$; tetradecamethylhexasiloxane ($MD_4M$) with a boiling point of 245° C. and a viscosity of 2.63 $mm^2/s$ represented by the formula $(CH_3)_3SiO((CH_3)_2SiO)_4Si(CH_3)_3$; and hexadecamethylheptasiloxane ($MD_5M$) with a boiling point of 270° C. and a viscosity of 3.24 $mm^2/s$ represented by the formula $(CH_3)_3SiO((CH_3)_2SiO)_5Si(CH_3)_3$. In addition, heptamethyloctyltrisiloxane shown by the formula $(CH_3)_3SiO((CH_3)(C_8H_{17})SiO)Si(CH_3)_3$ (MDRM) is exemplified as a representative methylalkylpolysiloxane having both terminal ends blocked with trimethylsiloxy-groups.

Some representative examples of the volatile cyclic methyl siloxanes include hexamethylcyclotrisiloxane (D3) with a boiling point of 134° C. represented by the formula $\{(CH_3)_2SiO\}_3$; octamethylcyclotetrasiloxane (D4) with a boiling point of 176° C., represented by the formula $\{(CH_3)_2SiO\}_4$; decamethylcyclopentasiloxane (D5) with a boiling point of 210° C., represented by the formula $\{(CH_3)_2SiO\}_5$; and dodecamethylcyclohexasiloxane (D6) with a boiling point of 245° C., represented by the formula $\{(CH_3)_2SiO\}_6$. Also, some representative examples of the branched volatile methyl siloxanes (IV) include heptamethyl-3-{(trimethylsilyl)oxy}trisiloxane with a boiling point of 192° C. and a viscosity of 1.57 $mm^2/s$, represented by the formula $CH_3Si\{OSi(CH_3)_3\}_3$ ($M^3T$); hexamethyl-3,3-propyl{(trimethysilyl)oxy}trisiloxane with a viscosity of 2.3 $mm^2/s$ represented by the formula $C_3H_7Si\{OSi(CH_3)_3\}_3$ ($M_3T$); hexamethyl-3,3-ethyl{(trimethylsilyl)oxy}trisiloxane represented by the formaula $C_2H_5Si\{OSi$ $(CH_3)_3\}_3(M_3)$; hexamethyl-3,3-bis{trimethylsilyl)oxy}trisiloxane with a boiling point of 222° C. and a viscosity of 2.86 mm²/s, represented by the formula $Si\{OSi(CH_3)_3\}_4$ $(M_4Q)$; as well as pentamethyl{(trimethylsilyl)oxy}cyclotrisiloxane represented by the formula $((CH_3)_2SiO)_2\{CH_3Si(OSi(CH_3)_3)O\}$. Among them, combinations between the aforementioned gelling agent and decamethylcyclopentasiloxane (D5) are particularly preferable in this invention.

The cosmetic of the present invention can further contain one, two, or more types of surfactants as ingredient (c) selected from the group comprising anionic surfactants, cationic surfactants, nonionic surfactants, amphoteric surfactants, and zwitterionic surfactants. To provide better detergent activity, the cosmetic preferably contain one or more surfactants.

More specifically, the anionic surfactants are exemplified by saturated or unsaturated fatty acid salts (for instance, sodium laurate, sodium stearate, sodium oleate, and sodium linoleate, etc.), alkylsulfuric acid salts, alkylbenzenesulfonic acids (for instance, hexylbenzenesulfonic acid, octylbenzenesulfonic acid, and dodecylbenzenesulfonic acid, etc.) and their salts, polyoxyalkylene alkyl ether sulfates, polyoxyalkylene alkenyl ether sulfates, polyoxyethylene alkyl sulfate ester salts, sulfosuccinic acid alkyl ester salts, polyoxyalkylenesulfosuccinic acid alkyl ester salts, polyoxyalkylene alkyl phenyl ether sulfates, alkanesulfonic acid salts, octyltrimethylammonium hydroxide, dodecyltrimethylammonium hydroxide, alkyl sulfonates, polyoxyethylene alkyl phenyl ether sulfates, polyoxyalkylene alkyl ether acetates, alkylphosphoric acid salts, polyoxyalkylene alkyl ether phosphates, acylglutamic acid salts, α-acylsulfonic acid salts, alkylsulfonic acid salts, alkylallylsulfonic acid salts, α-olefin sulfonates, alkylnaphthalenesulfonic acid salts, alkanesulfonic acid salts, alkyl- or alkenylsulfuric acid salts, alkylamide sulfates, alkyl- or alkenylphosphoric acid salts, alkylamide phosphates, alkyloylalkyltaurine salts, N-acylaminoacid salts, sulfosuccinic acid salts, alkyl ether carboxylates, amide ether carboxylates, alpha-sulfo fatty acid ester salts, alanine derivatives, glycine derivatives, and arginine derivatives. Sodium salts and other alkali metal salts, magnesium salts and other alkaline earth metal salts, triethanolamine salts and other alkanolamine salts, as well as ammonium salts are suggested as the salts.

The cationic surfactants are exemplified by alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2EO) chloride, benzalkonium chloride, alkyl benzalkonium chloride, alkyl dimethyl benzalkonium chloride, benzethonium chloride, stearyldimethylbenzylammonium chloride, lanolin-derived quaternary ammonium salt, stearic acid diethylaminoethylamide, stearic acid dimethylaminopropylamide, behenic acid amide propyldimethyl hydroxypropylammonium chloride, stearoycol aminoformyl methylpyridinium chloride, cetylpyridinium chloride, tall oil alkylbenzyl hydroxyethyl imidazolinium chloride, and benzylammonium salts.

The nonionic surfactants are exemplified by polyoxyalkylene ethers, polyoxyalkylene alkyl ethers, polyoxyalkylene fatty acid esters, polyoxyalkylene fatty acid diesters, polyoxyalkylene resinic acid esters, polyoxyalkylene (hydrogenated) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerin fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, diethylene glycols, polyoxyalkylene-modified silicones, polyglyceryl-modified silicones, glyceryl-modified silicones, saccharide-modified silicones, fluorine-containing surfactants, polyoxyethylene-polyoxypropylene block polymers, and alkyl polyoxyethylene-polyoxypropylene block polymer ethers. Adding polyoxyalkylene-modified silicones, polyglyceryl-modified silicones, glyceryl-modified silicones, and saccharide-modified silicones is particularly preferable. Since these modified silicones have the same silicone skeleton as the gelling agent of the present invention, using them in combination has the advantage of improving not only the cleansing power, but also the stability and gelatinous property of the cosmetic.

The amphoteric surfactants are exemplified by imidazoline type, amide betaine type, alkyl betaine type, alkyl amide betaine type, alkyl sulfobetaine type, amide sulfobetaine type, hydroxysulfobetaine type, carbobetaine type, phosphobetaine type, aminocarboxylic acid type, and amide aminoacid type amphoteric surfactants. Specifically, they are exemplified by sodiuim 2-undecyl-N,N,N-(hydroxyethylcarboxymethyl)-2-imidazoline, 2-cocoyl-2-imidazolinium hydroxide-1-carboxyethyloxy-2-sodium salt and other imidazoline type amphoteric surfactants; lauryldimethylaminoacetic acid betaine, myristyl betaine, and other alkyl betaine type amphoteric surfactants; palm oil fatty acid amide propyldimethylaminoacetic acid betaine, palm kernel oil fatty acid amide propyldimethylaminoacetic acid betaine, beef tallow fatty acid amide propyldimethylaminoacetic acid betaine, hydrogenated beef tallow fatty acid amidopropyldimethylaminoacetic acid betaine, lauric acid amide propyldimethylaminoacetic acid betaine, myristic acid amide propyldimethylaminoacetic acid betaine, palmitic acid amide propyldimethylaminoacetic acid betaine, stearic acid amide propyldimethylaminoacetic acid betaine, oleic acid amide propyldimethylaminoacetic betaine and amide betaine type amphoteric surfactants; coconut fatty acid dimethyl sulfopropyl betaine and other alkyl sulfobetaine type amphoteric surfactants; lauryl dimethylamino hydroxy sulfobetaine and other alkyl hydroxy sulfobetaine type amphoteric surfactants; lauryl hydroxy phosphobetaine and other phosphobetaine type surfactants; sodium N-lauroyl-N'-hydroxyethyl-N'-carboxymethylethylenediamine, sodium N-oleoyl-N'-hydroxyethyl-N'-carboxymethylethylenediamine, sodium N-cocoyl-N'-hydroxyethyl-N'-carboxymethylethylenediamine, potassium N-lauroyl-N'-hydroxyethyl-N'-carboxymethylethylenediamine, potassium N-oleoyl-N'-hydroxyethyl-N'-carboxymethylethylenediamine, sodium N-lauroyl-N-hydroxyethyl-N'-carboxymethylethylenediamine, sodium N-oleoyl-N-hydroxyethyl-N'-carboxymethylethylenediamine, sodium N-cocoyl-N-hydroxyethyl-N'-carboxymethylethylenediamine, monosodium N-lauroyl-N-hydroxyethyl-N'N'-dicarboxymethylethylenediamine, monosodium N-oleoyl-N-hydroxyethyl-N'N'-dicarboxymethylethylenediamine, monosodium N-cocoyl-N-hydroxyethyl-N'N'dicarboxymethylethylenediamine, disodium N-lauroyl-N-hydroxyethyl-N'N'-dicarboxymethylethylenediamine, disodium N-oleoyl-N-hydroxyethyl-N'N'-dicarboxymethylethylenediamine, disodium N-cocoyl-N-hydroxyethyl-N'N'- dicarboxymethylethylenediamine, and other amide amino acid type amphoteric surfactants.

The zwitterionic surfactants are exemplified by alkylamine oxide type surfactants, alkylamine oxides, alkylamide amine oxides, alkyl hydroxyamine oxides, etc., with C10-18 alkyl dimethylamine oxides and $C_{8-18}$ alkoxyethyl dihydroxyethylamine oxides being preferable. Specifically, they are exemplified by dodecyl dimethylamine oxide, dimethyl octylamine oxide, diethyl decylamine oxide, bis(2-hydroxyethyl) dodecylamine oxide, dipropyl tetradecylamine oxide, methylethyl hexadecylamine oxide, dodecylamidopropyl dimethylamine oxide, cetyl dimethylamine oxide, stearyl dimethylamine oxide, tallow dimethylamine oxide, dimethyl-2-hydroxy octadecylamine oxide, lauryl dimethylamine oxide, myristyl dimethylamine oxide, stearyl dimethylamine oxide, isostearyl dimethylamine oxide, cocoalkyl dimethylamine oxide, caprylic acid amidopropyl dimethylamine oxide, capric acid amidopropyl dimethylamine oxide, lauric acid amidopropyl dimethylamine oxide, myristic acid amidopropyl dimethylamine oxide, palmitic acid amidopropyl dimethylamine oxide, stearic acid amidopropyl dimethylamine oxide, isostearic acid amidopropyl dimethylamine oxide, oleic acid amidopropyl dimethylamine oxide, ricinoleic acid amidopropyl dimethylamine oxide, 12-hydroxystearic acid amidopropyl dimethylamine oxide, coconut fatty acid amidopropyl dimethylamine oxide, palm kernel oil fatty acid amidopropyl dimethylamine oxide, castor oil fatty acid amidopropyl dimethylamine oxide, lauric acid amidoethyl dimethylamine oxide, myristic acid amidoethyl dimethylamine oxide, coconut fatty acid amidoethyl dimethylamine oxide, lauric acid amidoethyl diethylamine oxide, myristic acid amidoethyl diethylamine oxide, coconut fatty acid amidoethyl diethylamine oxide, lauric acid amidoethyl dihydroxyethylamine oxide, myristic acid amidoethyl dihydroxyethylamine oxide, and coconut fatty acid amidoethyl dihydroxyethylamine oxide.

The cosmetic and cosmetic product of the present invention have the advantage of superior skin- and hair-cleansing performance, as well as the absence of stickiness and a refreshed sensory feel after face-washing, when they are various types of hair rinses, shampoos, and other hair cleansing agents, as well as skin cleansing agents, such as cleansing gels, cleansing creams, cleansing milk, cleansing lotions, face washes, etc. that contain ingredient (c) as a detergent agent. The amount of such ingredient (c) to be added in the present cosmetic is preferably 1 to 20 wt %, and even more preferably, 0.5 to 10 wt % based on the total amount of the cosmetic or cosmetic product.

The cosmetic of the present invention can further contain a powder and/or a colorant as ingredient (d). Although any type of such powders and/or colorants can be used in an ordinary cosmetic regardless of their shape (spherical, rod-shaped, needle-shaped, plate-shaped, amorphous, spindle-shaped, etc.) or their particle size (aerosol, microparticulate, pigment grades), or particle structure (porous, or without pores). When such powders and/or colorants are used as pigments, it is preferable to contain one, two, or more kinds of powders selected from inorganic pigment powders, organic pigment powders, and resin powders with a mean particle size in the range of from 1 nm to 20 μm.

For instance, inorganic powders, organic powders, surfactant metal salt powders (metal soaps), colored pigments, pearlescent pigments, metal powder pigments, etc. are suggested as the powders and/or colorants of ingredient (d), and materials obtained by hybridizing these pigments can be used as well. Specifically, titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, Lithia mica, silicic acid, anhydrous silicic acid, aluminium silicate, magnesium silicate, magnesium aluminium silicate, sodium silicate, magnesium sodium silicate, calcium silicate, barium silicate, strontium silicate, tungstic acid metal salts, hydroxyapatite, vermiculite, Higilite™, bentonite, montmorillonite, hectorite, zeolite, ceramic powder, calcium secondary phosphate, alumina, aluminium hydroxide, and boron nitride etc. are suggested as the inorganic powders; polyamide powder, polyester powder, polyethylene powder, polypropylene powder, polystyrene powder, polyurethane powder, benzoguanamine powder, polymethyl benzoguanamine powder, polytetrafluoroethylene powder, polymethyl methacrylate powder, cellulose, silk powder, nylon powder, Nylon 12, Nylon 6, silicone powder, silicone rubber powder, silicone elastomer spherical powder, polymethyl silsesquioxane spherical powder, styrene, acrylic acid copolymer, divinylbenzene, styrene copolymer, vinyl resin, urea resin, phenol resin, fluoroplastics, silicone, acrylic resin, melamine resin, epoxy resin, polycarbonate resin, microcrystal fiber powder, starch powder, lauroyl lysine, etc. are suggested as the organic powders; zinc stearate, aluminum stearate, calcium stearate, magnesium stearate, zinc myristate, magnesium myristate, zinc cetylphosphate, calcium cetylphosphate, and sodium zinc cetylphosphate are suggested as the surfactant metal salt powders; iron oxide, iron hydroxide, iron titanate, and other inorganic red pigment, gamma-iron oxide and other inorganic brown pigments, yellow iron oxide, loess, and other inorganic yellow pigments, black iron oxide, carbon blacks and other inorganic black pigments, manganese violet, cobalt violet and other inorganic purple pigments, chromium hydroxide, chromium oxide, cobalt oxide, cobalt titanate and other inorganic green pigments; titanium black, ultramarine blue and other inorganic blue pigments, Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and other coal tar based pigments, and pigments obtained by laking natural colorants, such as carminic acid, laccaic acid, carthamin, brazilin, and crocin are suggested as colored pigments; titanium oxide coated mica, titanium oxide, bismuth oxychloride, titanium oxide coated bismuth oxychloride, titanium oxide coated talc, fish scale flake, titanium oxide coated colored mica are suggested as the pearlescent pigments; and powders of aluminum, gold, silver, copper, platinum, stainless steel, and other metals are suggested as the metal powder pigments.

Furthermore, it is particularly preferable that a hydrophobic treatment is carried on the powders and/or colorants of ingredient (d). The gelling agent and gel composition used in the cosmetic of the present invention have the effect of preventing these water-repellent pigments from changing its position, and, as a result, makes it possible to improve makeup hold and makeup durability. In addition, the gelling agent of the present invention is capable of absorbing not only various oily substances, but also skin fats, thereby making it possible to improve the resistance of the cosmetic to skin fats.

Examples of such hydrophobic treatments include treating the powders and/or colorants with various hydrophobicity-inducing surface treatment agents, for instance, such as in case of methylhydrogenpolysiloxane treatment, silicone resin treatment, silicone gum treatment, acryl silicone treatment, fluorinated silicone treatment, and other types of organosiloxane treatment, zinc stearate treatment, and other types of metal soap treatment, silane coupling agent treatment, alkyl silane treatment, and other types of silane treatment, perfluoroalkylsilane, perfluoroalkylphosphoric acid ester salt, perfluoropolyether treatment, and other types of fluorine compound treatment, N-lauroyl-L-lysine treatment, and other types of amino acid treatment, squalane treatment and other types of oil substance treatment, alkyl acrylate treatment and other types of acrylic treatment. These treatments may be used either singly or as a combination of two or more treatments.

The cosmetic of the present invention can further contain a water soluble polymer as ingredient (e). When such water soluble polymers are used to improve the in-use sensory feel of the cosmetics, any of amphoteric polymers, cationic polymers, anionic polymers, nonionic polymers, and expansive clay materials can be utilized. These water-soluble polymers may be used either singly or as a combination of two or more polymers.

The amphoteric water-soluble polymers are exemplified by amphoteric starch, dimethyl diallyl ammonium chloride derivatives (for instance, copolymers of acrylamide, acrylic acid, and dimethyl diallyl ammonium chloride, copolymers of acrylic acid and dimethyl diallyl ammonium chloride), methacrylic acid derivatives (for instance, copolymers of alkyl methacrylate and N-methacryloyloxyethyl-N,N-dimethylammonium-a-methylcarboxybetaine, and polymethacryloylethyldimethylbetaine).

The cationic water-soluble polymers are exemplified by quaternary nitrogen-modified polysaccharides (for instance, cation-modified cellulose, cation-modified hydroxyethyl cellulose, cation-modified guar gum, cation-modified locust bean gum, cation-modified starch, etc.), dimethyl diallyl ammonium chloride derivative (for instance, dimethyl diallyl ammonium chloride/acrylamide copolymer, polydimethylmethylenepiperidinium chloride, etc.), vinylpyrrolidone derivatives (for instance, vinylpyrrolidone/dimethylaminoethylmethacrylic acid copolymer salts, vinylpyrrolidone/methacrylamidopropyltrimethylammonium chloride copolymer, vinylpyrrolidone/methylvinylimidazolium chloride copolymer, etc.), and methacrylic acid derivatives (for instance, methacryloyl ethyl dimethyl betaine/methacryloylethyltrimethylammonium chloride/2-hydroxyethyl methacrylate copolymer, methacryloyl ethyl dimethyl betaine/methacryloyl ethyl trimethylammonium chloride/methoxypolyethylene glycol methacrylate copolymer, etc.)

The anionic water-soluble polymers are exemplified by polyacrylic acid or its alkali metal salts, polymethacrylic acid or its alkali metal salts, hyaluronic acid or its alkali metal salts, acetylated hyaluronic acid or its alkali metal salts, water soluble polymers of aliphatic carboxylic acids such as hydrolyzate of methyl vinyl ether-maleic anhydride copolymer or their metal salts, carboxymethylcellulose or its alkali metal salts, methyl vinyl ether/maleic acid half ester copolymer, acrylic resin alkanolamine solutions, and carboxyvinyl polymers.

The nonionic water-soluble polymers are exemplified by polyvinyl pyrrolidone, highly polymerized polyethylene glycol, vinylpyrrolidone/vinyl acetate copolymer, vinylpyrrolidone/dimethylaminoethyl methacrylate copolymer, vinyl caprolactam/vinylpyrrolidone/dimethylaminoethyl methacrylate copolymer, cellulose or its derivatives (for instance, methyl cellulose, ethyl cellulose, hydroxyethyl cellulose, hydroxypropyl cellulose, and carboxymethyl cellulose), keratin, collagen or their derivatives, calcium alginate, pullulan, agar-agar, gelatin, tamarind seed polysaccharides, xanthan gum, carrageenan, high-methoxyl pectin, low-methoxyl pectin, guar gum, pectin, gum arabic, crystalline cellulose, arabinogalactan, gum Karaya, tragacanth gum, alginic acid, albumin, casein, curdlan, gellan gum, dextran, quince seed gum, tragranth gum, chitin-chitosan derivatives, starches (rice, corn, potato, and wheat, etc.), and other natural polymer compounds.

The expansible clay minerals are inorganic water soluble polymers constituting a type of colloid-containing aluminum silicate with a three-layer structure, exemplified by the following formula:

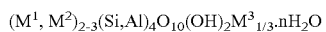

(where $M^1$ is Al, Fe (III), Mn (III), or Cr (III), $M^2$ is Mg, Fe (II), Ni, Zn, or Li, and $M^3$ is K, Na, or Ca).

Such inorganic water soluble polymers are specifically exemplified by bentonite, montmorillonite, pyderite, nontronite, saponite, hectorite, magnesium aluminum silicate, and anhydrous silicic acid, which may be either natural or synthetic clay minerals.

The amount of such ingredient (e) is preferably 0.01 to 25.0 wt % based on the total amount of the cosmetic or cosmetic product. When the amount is below the above-mentioned lower limit, the coating properties of the cosmetic become insufficient, and exceeding the upper limit leads to increased stickiness, which is generally undesirable in cosmetics.

The cosmetic of the present invention can further contain one, two, or more types of silicone resins as ingredient (f). So long as the object of the present invention is not impaired, any silicone resins normally used in cosmetics can be utilized as such silicone resins, with one or more compounds selected from trimethylsiloxysilicic acid, polyalkylsiloxysilicic acid, dimethylsiloxy unit-containing trimethylsiloxysilicic acid, perfluoroalkyl group-containing polyalkylsiloxysilicic acid, polydimethylsiloxane graft type acrylic copolymers, and branched carboxysiloxane dendrimer graft type acrylic copolymers being particularly preferable. These silicone resins are gum-like or solid, and, preferably, oil-soluble. It is particularly preferable that the silicone resins are soluble in octamethyltetrasiloxane (D4) and/or decamethylcyclopentasiloxane (D5).

Specifically, as far as the gum-like silicones are concerned, in linear silicones represented by the general formula $(CH_3)_3SiO\{(CH_3)_2SiO\}_a\{(CH_3)R^3SiO\}_bSi(CH_3)_3$, $R^3$ is preferably selected from methyl, $C_{6-20}$ alkyl groups, $C_{3-15}$ amino-containing alkyl groups, fluorine-substituted alkyl groups, or quaternary ammonium salt-containing alkyl groups, with the subscript <<a>> preferably being in the range of from 1 to 5000, and <<a+b>> being in the range of from 2500 to 25000.

The solid silicones are preferably the cross-linked silicone compounds, such as MQ resins, MDQ resins, MTQ resins, MDT resins, TD resins, TQ resins, and TDQ resins comprising trialkylsiloxy units (M units), dialkylsiloxy units (D units), monoalkylsiloxy units (T units), tetrafunctional siloxy units (Q units) in arbitrary combinations. Furthermore, it is particularly preferable for the silicones to be polydimethylsiloxane graft type and branched carbosiloxane dendrimer graft type acrylic copolymers containing at least one moiety selected from the group comprising carboxylic acid alkyl esters, pyrrolidone moieties, long-chain alkyl moieties, polyoxyalkylene moieties, as well as fluoroalkyl moieties, carboxylic acid and other anionic moieties in one molecule. The branched carbosiloxane dendrimer graft alkyl copolymers are exemplified by compounds described in Japanese Unexamined Laid-Open Patent Application No. 2000-063225 and in Japanese Unexamined Laid-Open Patent Application No. 2003-226611, etc.

These silicone resins may be added to the cosmetic alone, but it is also possible to add them as solutions in volatile silicones, volatile hydrocarbon oils, nonvolatile silicones, and nonvolatile hydrocarbon oils. The amount of such silicone resins is preferably in the range of from 0.1 to 20 wt %, and even more preferably, in the range of from 1 to 10 wt % based on the total amount of the cosmetic. In addition, to obtain cosmetics having high adhesive properties to the skin, it is preferable to use cosmetic compositions containing 50 to 500 parts by weight of the silicone resins per 100 parts by weight of the silicone gelling agent of the present invention.

The cosmetic of the present invention can further contain silicone elastomers as ingredient (g). The term "silicone elastomer" refers to highly polymerized organopolysiloxane compounds, whose principal chain consists of a three-dimensionally cross-linked methylpolysiloxane skeleton. And the silicone elastomers may be as a spherical or oblate granular form or as shapeless oil dispersions. In the present invention, it is preferable to use silicone elastomers having a particulate form, wherein the mean primary particle size is in the range of from 0.1 to 50 μm, measured by laser diffraction/scattering methods and/or obtained by observation under an electron microscope. In addition, the JIS Type A durometer hardness of the silicone elastomers is preferably not more than 80, and, more preferably, not more than 65.

One method suggested for silicone elastomer preparation consists in reacting a cross-linking agent having vinylic reaction sites with an alkylhydrogenpolysiloxane having two or more silicone-bonded hydrogen atoms in the presence of chloroplatinic acid and other catalysts. The cross-linking agents, which form three-dimensionally cross-linked structures in the silicone elastomers of the present invention, have two or more vinylic reaction sites in a molecule, as in alkenyl-functional organopolysiloxanes, α,ω-alkenyldienes, glycerin triallyl ether, polyoxy alkenylated glycerin triallyl ether, trimethylolpropane triallyl ether, polyoxy alkynylated trimethylolpropane triallyl ethers, etc.

Such silicone elastomers are described, for instance, in Japanese Unexamined Laid-Open Patent Application Publication No. H02-243612, H08-12545, H08-12546, H08-12524, H09-241511, H10-36219, H11-193331, 2000-281523 etc., and, specifically, correspond to cross-linked silicone powders listed in the "Keshouhin Shubetsu Haigou Seibun Kikaku" ("Standards for Various Types of Cosmetic Ingredients"), such as Trefil E-505, 506, 507, 508 and other products in the Trefil E-series available from Dow Corning Toray Co., Ltd. In addition, the surface of the powders may be treated or untreated, with methylhydrogenpolysiloxane, silicone resins, metal soaps, silane coupling agents, silica, titanium oxide and other inorganic oxides, perfluoroalkylsilanes, perfluoroalkylphosphoric acid ester salts and other fluorine compounds suggested as examples of possible surface treatments.

Furthermore, the powders may be combined with the formulation in one or more forms selected from materials obtained by mixing granular-shaped silicone elastomers with oil substances, materials obtained by finely dividing them using a crusher, or aqueous dispersions thereof. More specifically, suggested methods include adding them in the form of paste-like materials obtained by mixing or finely dividing silicone elastomers with one, two, or more oil ingredients liquid at room temperature, selected from the group comprising ester oils, hydrocarbon oils, higher alcohols, vegetable oils, and animal fats; adding silicone elastomers after mechanically crushing and inhibiting agglutination; and adding silicone elastomers after mechanically crushing and dispersing them in water using mechanical force.

While spherical silicone elastomer powders often have particle sizes exceeding 10 μm and are difficult to bond to the skin, using them in combination with the gelling agent and the gel composition of the present invention has the advantage of permitting formation of stable coating films. Furthermore, since these powders scatter light, cosmetics containing them sometimes had a matte finish, but because the gelling agent of the present invention can provide a coating consisting of a glossy film, it is capable of imparting more glossiness to cosmetic coating films in comparison with cases, in which the agent is not added. The amount of organopolysiloxane elastomer is preferably 0.1 to 30 mass % relative to the mass of the cosmetic of this invention. When it is less than the above-mentioned lower limit, decreased water slippage becomes a problem, and when it exceeds the above-mentioned upper limit, good water slippage is obtained, but the physical strength of the coating film deteriorates and it becomes relatively vulnerable to physical contact etc.

The cosmetic of the present invention can further contain UV-ray protective component as ingredient (h). In this invention, inorganic and organic UV-ray protective component can be preferably formulated as ingredient (h) in the cosmetics.

The inorganic UV-ray protective component may contain the above-mentioned inorganic powder pigments, metal powder pigments, etc. as UV light dispersers including titania, zinc oxide, cerium oxide, titanium suboxide, iron-doped titanium oxide and other metal oxides, iron hydroxides and other metal hydroxides, platy iron oxide, aluminum flake, and other metal flakes, silicon carbide and other ceramics. Among them, at least one type of material selected from metal oxide particulates or metal hydroxide particulates with a mean particle size in the range of from 1 to 100 nm is particularly preferable. These powders are preferably surface treated using conventional surface treatment techniques including, for instance, fluorine compound treatment (perfluoroalkyl phosphate treatment, perfluoroalkylsilane treatment, perfluoropolyether treatment, fluorosilicone treatment, and fluorinated silicone resin treatment are preferable), silicone treatment (methylhydrogenpolysiloxane treatment, dimethylpolysiloxane treatment, and vapor-phase tetramethyltetrahydrogencyclotetrasiloxane treatment are preferable), silicone resin treatment (trimethylsiloxysilicic acid treatment is preferable), pendant treatment (the method of adding alkyl chains etc. after vapor-phase silicone treatment), silane coupling agent treatment, titanate coupling agent treatment, silane treatment (alkyl silane and alkyl silazane treatment are preferable), oil solution treatment, N-acylated lysine treatment, polyacrylic acid treatment, metal soap treatment (stearic acid and myristic acid salts are preferable), acrylic resin treatment, metal oxide treatment, etc., and, even more preferably, treated using a combination of several types of treatment. For instance, it is suggested that, after coating the surface of the titanium oxide particulate with silicon oxide, alumina and other metal oxides, the powder can be surface treated with alkyl silane. The total amount of material used for surface treatment is preferably in the range of from 0.1 to 50 mass % based on the mass of the powder.

The organic UV-ray protective components are exemplified by homomethyl salicylate, octyl salicylate, triethanolamine salicylate, and other salicylic acid derived ingredients; para-aminobenzoic acid, ethyldihydroxypropyl para-aminobenzoate, glyceryl para-aminobenzoate, octyl dimethyl para-aminobenzoate, amyl para-dimethylaminobenzoate, 2-ethylhexyl para-dimethylaminobenzoate, and other PABAtype ingredients; 4-(2-β-glucopyranosyloxy)propoxy-2-hydroxybenzophenone, dihydroxy dimethoxy benzophenone, sodium dihydroxydimethoxybenzophenone disulphonate, 2-hydroxy-4-methoxybenzophenone, hydroxymethoxybenzophenone sulfonic acid and its trihydrates, sodium hydroxymethoxybenzophenone sulfonate, 2-hydroxy-4-methoxybenzophenone-5-sulfuric acid, 2,2'-dihydroxy-4-methoxy benzophenone, 2,4-dihydroxybenzophenone, 2,2',4,4'-tetrahydroxy benzophenone, 2,2'-dihydroxy-4,4'-dimethoxy benzophenone, 2-hydroxy-4-N-octoxy benzophenone, and other benzophenone-type ingredients; 2-ethylhexyl para-methoxycinnamate (also called octyl para-methoxycinnamate), glyceryl di-para methoxycinnamate, mono-2-ethylhexanoatemethyl 2,5-diisopropylcinnamate, 2,4,6-tris[4-(2-ethylhexyloxycarbonyl)anilino]-1,3,5-triazine, methylbis(trimethylsiloxy)silylisopentyl trimethoxycinnamateisoproyl para-methoxycinnamate/diisopropylcinnamic acid ester mixture, p-methoxyhydrocinnamic acid diethanolamine salt, and other cinnamic acid type ingredients; 2-phenyl-benzimidazole-5-sulfuric acid, 4-isopropyldibenzoylmethane-4-tert-butyl-4'-methoxydibenzoylmethane, and other benzoyl methane series ingredients; 2-cyano-3,3-diphenylpropane-2-enoic acid 2-ethylhexyl ester (also called octocrylene), 2-ethylhexyl dimethoxybenzylidene oxoimidazolidinepropionate, 1-(3,4-dimethoxyphenyl)-4,4-dimethyl-1,3-pentanedione, cinoxate, methyl-o-aminobenzoate, 2-ethylhexyl-2-cyano-3,3-diphenyl acrylate, 3-(4-methylbenzylidene)camphor, octyltriazone, 2-ethylhexyl 4-(3,4-dimethoxyphenylmethylene)-2,5-dioxo-1-imidazolidine propionate, as well as polymeric derivatives and silane derivatives thereof, etc.

Furthermore, the above-mentioned organic UV-ray protective components can be sealed inside the polymer powder. The polymer powder may be hollow or not, with its mean primary particle size being in the range of from 0.1 to 50 μm, and its particle size distribution being either broad or sharp. Suggested polymer types include acrylic resins, methacrylic resins, styrene resins, polyurethane resins, polyethylene, polypropylene, polyethylene terephthalate, silicone resins, nylons, acrylamide resins, etc. It is preferable to use powders obtained by combining these polymer powders with organic UV-ray protective components in the range of from 0.1 to 30 mass % relative to the mass of the powder, and adding 4-tert-butyl-4'-methoxydibenzoyl methane, which is a UV-A absorber, is particularly preferable.

At least one UV-ray protective component can suitably used from the group comprising titanium oxide particulate, zinc oxide particulate, 2-ethylhexyl para-methoxycinnamate, 4-tert-butyl-4'-methoxydibenzoyl methane, and benzophenone-type UV absorbers since they are commonly used, easy to be obtained and have excellent UV light-protective effects. Using inorganic and organic UV-ray protective components together is especially preferable, and using UV-ray protective components designed for UV-A and UV-ray protective components designed for UV-B in combination is even more preferable.

The amount of the UV-ray protective components in the cosmetic of the present invention is preferably in the range of from 0.1 to 60 mass %, and particularly preferably, in the range of from 3 to 40 mass % based on the mass of the cosmetic. Furthermore, the amount of the inorganic UV-ray protective components is preferably in the range of from 0.1 to 30 mass % based on the mass of the cosmetic, the amount of the added organic UV-ray protective components is preferably in the range of from 0.1 to 20 mass % based on the mass of the cosmetic, and, when combined therewith, the amount of the added ingredient (a) (gelling agent of this invention) is preferably in the range of 0.1 to 20 mass % based on the mass of the cosmetic. The resultant UV-ray protective effects last longer in comparison with cases, in which the gelling agent of the present invention is not added in the specific range suitable for these combinations. Furthermore, adding the aforementioned gelling agent and gel composition can provide excellent moisture retention effects to the formulation itself and can provide superior curl retention, a lustrous feel and facilitate styling in hair cosmetics.

The cosmetic of the present invention may further contain conventional cosmetic ingredients such as antiseptics, bioactive ingredients, pH adjusters, antioxidants, solvents, chelating agents, moisturizing agents, fragrances, etc. so long as these ingredients does not impair the object of the present invention. These ingredients can be added to the cosmetic in the form of gel compositions formed by dissolving them in the above-mentioned ingredient (b) and can also be added to the cosmetic separately from the gelling agent or the gel composition.

The antiseptics are exemplified by paraoxybenzoic acid alkyl ester, benzoic acid, sodium benzoate, sorbic acid, potassium sorbate, phenoxyethanol, etc. In addition, the antibacterial agents are exemplified by benzoic acid, salicylic acid, carbolic acid, sorbic acid, paraoxybenzoic acid alkyl esters, parachlormethacresol, hexachlorophene, benzalkonium chloride, chlorhexidine chloride, trichlorocarbanilide, trichlosan, light-sensitive ingredients, phenoxyethanol, etc.

Substances imparting a certain physiological activity to the skin when applied to the skin are suggested as the bioactive ingredients used in the present invention. Anti-inflammatory agents, age inhibitors, astringent agents, anti-oxidants, hair-growing tonics, hair tonics, moisture-retaining agents, circulation-accelerating agents, antibacterial agents, sterilizers, desiccants, algefacient agents, calorifacient agents, vitamins, amino-acids, wound healing-accelerating agents, irritation reducers, analgesics, cell activators, enzymatic ingredients, etc. are suggested as examples. Among them, ingredients such as natural vegetable extracts, seaweed extracts, and herbal medicines are particularly preferable. In the present invention, it is preferable to add one, two, or more types of these physiologically active ingredients.

Example of these bioactive ingredients are as follow:
*Angelica keiskei* extract, avocado extract, *Hydrangea serrata* extract, Althea extract, *Arnica* extract, aloe extract, apricot extract, apricot kernel extract, *Gingko biloba* extract, Fennel fruit extract, Turmeric root extract, Oolong tea extract, *Rosa multiflora* extract, *Echinacea angustifolia* leaf extract, *Scutellaria baicalensis* root Extract, *Phellodendron amurense* extract, Coptis rhizome extract, *Hordeum vulgare* seed extract, *Hypericum perforatum* extract, Lamium album extract, *Nasturtium officinale* extract, orange extract, dried sea water solution, seaweed extract, hydrolyzed elastin, hydrolyzed wheat fines, hydrolyzed silk, Chamomile extract, carrot extract, *Artemisia capillaris* flower extract, Licorice extract, Karkade extract, *Pyracantha fortuneana* extract, kiwi extract, *Cinchona* extract, cucumber extract, guanosine, *Gardenia florida* extact, *Sasa veitchii* extract, *Sophora angustifolia* extract, walnut extract, grapefruit extract, *Clematis vitalba* leaf extract, *chlorella* extract, *Morus alba* root extract, *Gentiana lutea* extract, black tea extract, yeast extract, burdock extract, fermented rice bran extract, rice germ oil, Comfrey extract, collagen, Vaccinum *vitis idaea* extract, *Asiasarum* root extract, *Bupleurum falcatum* extract, umbilical extract, Salvia extract, Soapwort extract, Sasa bamboo grass extract, *Crataegus cuneata* fruit extract, *Zanthoxylum piperitum* extract, Shiitake extract, *Rehmannia* root extract, *Lithospermum erythrorhizone* root extract, *Perilla ocymoides* extract, *Tilia cordata* flower extract, *Spiraea ulmaria* extract, *Paeonia albiflora* extract, *Acorus calamus* root extract, *Betula alba* extract, *Equisetum arvense* extract, Hedera helix extract, *Crataegus oxyacantha* extract, *Sambucus nigra* extract, *Achillea millefolium* extract, *Mentha piperita* leaf extract, Sage extract, *Malva sylvestris* extract, *Cnidium officinale* root extract, *Swertia japonica* extract, Soybean extract, *Zizyphus jujuba* fruit extract, thyme extract, tea extract, *Eugenia caryophyllus* flower extract, *Imperata cylindrica* extract, *Citrus unshiu* Marc. extract, *Angelica* root extract, *Calendula officinalis* extract, *Prunus persica* stone extract, Citrus aurantium peel extract, *Houttuynia cordata* extract, tomato extract, natto extract, carrot extract, garlic extract, *Rosa canina* fruit extract, Hibiscus extract, Ophiopogon extract, Nelumbo nucifera extract, parsley extract, honey, Witch hazel extract, *Parietaria officinalis* extract, Isodon trichocarpus extract, bisabolol, *Eriobotrya japonica* extract, Coltsfoot flower extract, *Petasites japonicus* extract, *Poria cocos* extract, Butcher's broom extract, grape extract, propolis, *Luffa cylindrica* fruit extract, Safflower flower extract, peppermint extract, *Tillia miquellana* extract, *Paeonia suffruticosa* root extract, hops extract, *Pinus sylvestris* cone extract, horse chestnut extract, Japanese skunk-cabbage extract, *Sapindus mukurossi* peel extract, Melissa extract, peach extract, Centaurea cyanus flower extract, Eucalyptus extract, Saxifraga sarementosa extract, Citrus junos extract, *Coix* seed extract, *Artemisia princeps* extract, lavender extract, apple extract, lettuce extract, lemon extract, *Astragalus sinicus* extract, rose extract, rosemary extract, Roman chamomile extract, and royal jelly extract.

In addition, example of the bioactive ingredients are as follow: deoxyribonucleic acid, mucopolysaccharides, sodium hyaluronate, sodium chondroitin sulfate, collagen, elastin, chitin, chitosan, hydrolyzed eggshell membrane and other biopolymers etc., glycine, valine, leucine, isoleucine, serine, threonine, phenylalanine, arginine, lysine, aspartic acid, glutamate, cystine, cysteine, methionine, tryptophan and other amino acids, estradiol, ethenyl estradiol and other hormones, sphingolipids, ceramides, cholesterol, cholesterol derivatives, phospholipids and other oily ingredients, ε-aminocaproic acid, glycyrrhizinic acid, lysozyme chloride, guaiazulene, hydrocortisone, allantoin, tranexamic acid, azulene and other anti-inflammatory agents, vitamins A, B2, B6, C, D, and E, calcium pantothenate, biotin, nicotinic-acid amide, vitamin C ester, and other vitamins, allantoin, diisopropylamine dichloroacetate, 4-aminomethyl cyclohexanecarboxylic acid and other active ingredients, tocopherol, carotinoids, flavonoids, tannins, lignans, saponins, butylated hydroxyanisole, dibutylhydroxytoluene, phytic acid and other anti-oxidants, α-hydroxy acids, β-hydroxy acids, and other cell activators, γ-orizanol, vitamin E derivatives, and other circulation-accelerating agents, retinol, retinol derivatives, and other wound healing agents, cepharanthin, cayenne tincture, hinokitiol, iodized garlic extract, pyridoxine hydrochloride, dl-α-tocopherol, dl-α-tocopherol acetate, nicotinic acid, nicotinic acid derivatives, calcium pantothenate, D-pantothenyl alcohol, acetyl pantothenyl ethyl ether, biotin, allantoin, isopropyl methyl phenol, estradiol, ethynyl estradiol, capronium chloride, benzalkonium chloride, diphenhydramine hydrochloride, Takanal™, camphor, salicylic acid, nonylic acid vanillylamide, nonanoic acid vanillylamide, Piroctone olamine, glyceryl pentadecanoate, 1-menthol, camphor and other algefacient agents, mononitroguaiacol, resorcin, γ-aminobutyric acid, benzethonium chloride, mexiletine hydrochloride, auxin, female hormones, cantharis tincture, cyclosporine, zinc pyrithione, hydrocortisone, minoxidil, polyoxyethylene sorbitan monostearate, peppermint oil, and sasanishiki extract.

Example of the pH adjusters include Lactic acid, citric acid, glycolic acid, succinic acid, tartaric acid, d1-malic acid, potassium carbonate, sodium hydrogencarbonate, ammonium hydrogencarbonate, etc. Example of the chelating agents include alanine, sodium salt of edetic acid, sodium polyphosphate, sodium metaphosphate, and phosphoric acid.

In addition to purified water, mineral water, and other types of water, examples of the solvents include light liquid isoparaffin, ethers, LPG, N-methylpyrrolidone, next-generation chlorofluorocarbons, etc.

Example of the anti-oxidants include Tocopherol, butylated hydroxyanisole, dibutylhydroxytoluene, phytic acid, etc.

Example of the moisturizing agents include glycerin, sorbitol, propylene glycol, dipropylene glycol, 1,3-butylene glycol, glucose, xylitol, maltitol, polyethylene glycol, hyaluronic acid, chondroitin sulfate, carboxylate acid salts of pyrrolidone, polyoxyethylene methylglucoside, and polyoxypropylene methylglucoside, etc.

The cosmetic of the present invention is exemplified by skin cosmetic products, such as skin cleansing products, skin care products, makeup products, antiperspirant products, and UV-ray protective products, etc.; by hair cosmetic products, such as hair cleansing products, hair styling products, hair dyeing products, hair maintenance products, hair rinse products, etc; and by bath cosmetic products. Furthermore, since the gel composition of the present invention possesses superior transparency and lipophilic property, it can be readily added to various perfumes and colognes.

The skin cosmetic products mentioned above can be used in various locations, such as on the scalp, face (including lips, eyebrows, cheeks), fingers, nails, and the entire body. Specifically, such products are exemplified by cleansing gel, cleansing cream, cleansing foam, cleansing milk, cleansing lotion, facial cleansing cream, eye make-up remover, cleansing foam, liquid whole-body soap, hand soap, gel soap, bar soap, facial rinse, body rinse, shaving cream, nail polish remover, anti-acne skin cleansing products, skin cream, hot oil treatment for the scalp, skin milk, milk lotion, emulsion, toilet water, moisturizers, beauty liquid, facial compact powder, body powder, essences, shaving lotions and other skin care products; foundation, make-up base, white powder, face powder, lipstick, lip cream, lip color, lip-gloss, eye shadow, eyeliner, eye cream, eyebrow pencil, eyelash cosmetic products, eyebrow pencil, eyebrow brush, mascara, rouge, cheek cosmetic products (cheek color, cheek rouge), nail polish, toe polish, nail color, nail lacquer, enamel remover, and other makeup products; deodorants and other antiperspirants; sunscreen, suntanning drugs (suntanning agents) and other UV light protective products.

The hair care cosmetic products are exemplified by hair cleansing agents, such as shampoo, shampoo with rinse, etc.; hair oil, hair curl retaining agents, setting agents, hair cream, hair spray, hair liquid, and other hair styling products; hair dyes, hair color spray, hair color rinse, hair color stick, and other hair coloring products; hair tonic, hair treatment, hair balm, and other hair maintenance products; and oil rinse, cream rinse, treatment rinse, and other hair rinse products. In addition the above-mentioned bath cosmetic products are exemplified by bath oil, bath salts, foam bath products.

There are no particular limitations concerning the form of the cosmetics and cosmetic products of the present invention, which are suitably used as liquids, W/O emulsions, O/W emulsions, W/O creams, O/W creams, solids, pastes, gels, powders, multi-layered materials, mousses, mists, granular materials, flaky materials, or crushed materials. In particular, the aforementioned gelling agent makes it possible to obtain emulsion- and cream-like cosmetics of superior temporal stability since the oil-layer portion has increased viscosity or is gelled.

There are no restrictions concerning containers used for the cosmetics and cosmetic products of the present invention, which may be filled in any kind of containers, such as jars, pump cans, tubes, bottles, pressure spray containers, pressure-resistant aerosol containers, light-resistant containers, compact containers, metal cans, lipstick containers, dispensing containers, aerosol containers, partitioned containers with mixed fluid discharge outlets, etc. While conventional silicone formulations tend to separate when filled in tubes, the cosmetics and cosmetic products of the present invention offer the advantage of stable storage in such tube containers due to their superior temporal stability.

EXAMPLES

The invention will be further described in more detail with reference to reference examples and practical examples, though it should be understood that these examples should not be construed as limiting the scope of possible applications of the invention. In the examples, Me designates methyl groups. The following methods were used for measuring refractive index of the gelantinous products.

[Refractive Index]

The refractive index of the gelatinous compositions was measured at 25° C. by means of an ABBE refractometer (Type ER-1) produced by ERMA Inc.

Synthesis Example 1

Gelling Agent No. 1

A mixture was prepared from 30 g (11.0 mmol of NH2 groups) of a copolymer of methyl (3-aminopropyl) siloxane and dimethylpolysiloxane represented by the following average structural formula:

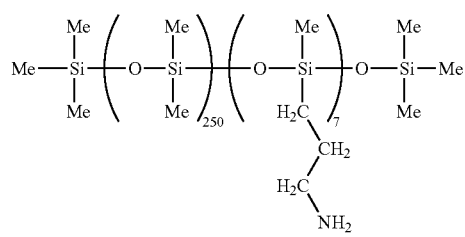

and 1.10 g (11.0 mmol) of an anhydrous succinic acid, which were both mixed in 36 g of isopropyl alcohol. The mixture was stirred for 5 hr at 30 to 35° C. Results of infrared (IR) analysis showed that specific absorption of carboxylic anhydride was lost, and that specific absorption of amide groups and carboxylic groups was detected. This confirmed that the obtained product was comprised of an modified methylpolysiloxane of the following average structural formula:

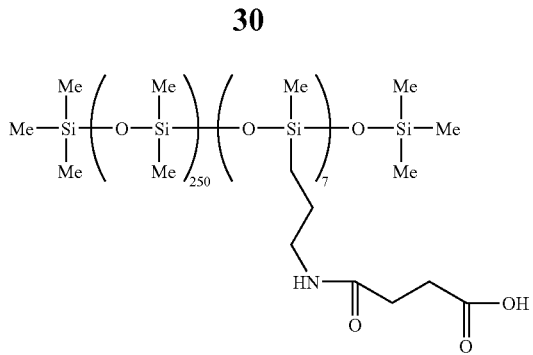

The obtained reaction product was further combined with 2.2 g (10.8 mmol) of a 20 wt. % aqueous solution of sodium hydroxide, and a reaction was carried out for 30 min. at 25° C. Following this, hexane was introduced and the solution was mixed uniformly. And, volatile contents were removed by distillation with heating in vacuum. As a result, a white solid substance (e.g. Gelling agent No. 1) was obtained. IR analysis showed that the obtained white solid substance was comprised of organically-modified methylpolysiloxane having carboxylic acid sodium salts on terminals of a silicon-bonded organic group and represented by the following formula:

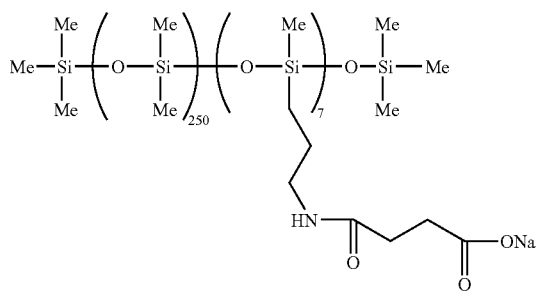

Synthesis Example 2

Gelling Agent No. 2

A mixture was prepared from 10 g (2.82 mmol of $NH_2$ groups) of a copolymer of a methyl (3-2-aminoethyl aminopropyl) siloxane and dimethylpolysiloxane represented by the following average structural formula:

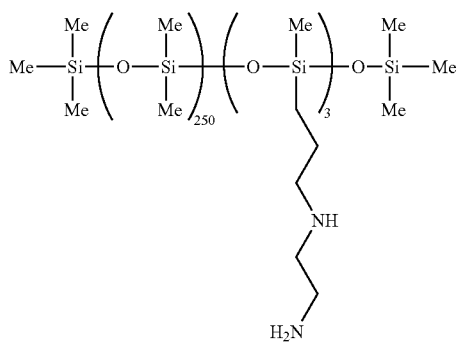

and 0.28 g (2.82 mmol) of an anhydrous succinic acid, which were both mixed in 20 g of isopropyl alcohol. The mixture was stirred for 5 hr at 30 to 40° C. Results of infrared (IR)

analysis showed that specific absorption of carboxylic anhydride was lost, and that specific absorption of amide groups and carboxylic groups was detected. The obtained reaction product was cooled to the room temperature and further combined with 0.56 g (2.79 mmol) of a 20 wt. % aqueous solution of sodium hydroxide, and a reaction was carried out for 30 min at room temperature. Following this, hexane was introduced and the solution was mixed uniformly. And, volatile contents were removed by distillation with heating in vacuum. As a result, a white solid substance (e.g. Gelling agent No. 2) was obtained. IR analysis showed that the obtained white solid substance was comprised of organically-modified methylpolysiloxane having carboxylic acid sodium salts on terminals of a silicon-bonded organic group and represented by the following formula:

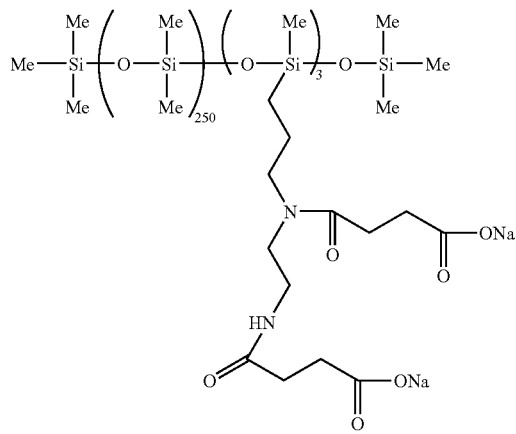

Synthesis Example 3

Gelling Agent No. 3

A reaction and mixing was carried out under the same conditions as in Synthesis Example 2, but using 0.784 g (2.79 mmol) of 20 wt. % aqueous solution of potassium hydroxide in place of 20 wt. % aqueous solution of sodium hydroxide, and a white solid substance (e.g. Gelling Agent No. 3) of an organically-modified methylpolysiloxane represented by the formula given below was obtained.

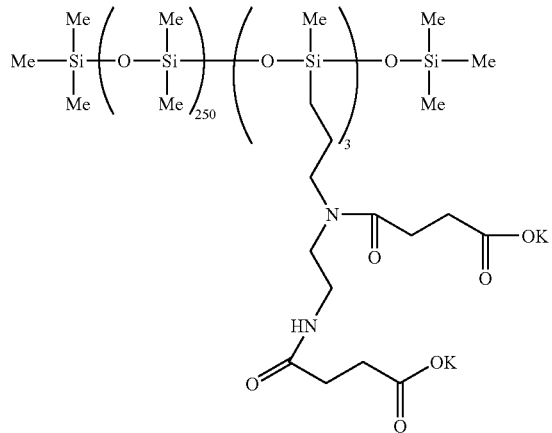

Synthesis Example 4

Gelling Agent No. 4 (for Comparative Examples)

A mixture was prepared from 20 g of carboxylic acid functional methylpolysiloxane represented by the following average structural formula:

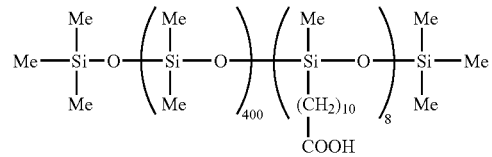

and 1.0 g (5.19 mmol) of a 20 wt. % aqueous solution of sodium hydroxide, which were both mixed in 20 g of isopropyl alcohol, and a reaction was carried out for 30 min. at room temperature. Following this, hexane was introduced and the solution was mixed uniformly. And, volatile contents were removed by distillation with heating in vacuum. As a result, a white solid substance (e.g. Gelling agent No. 4) was obtained.

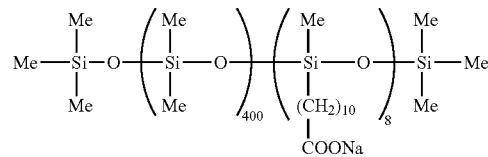

Synthesis Example 5

Gelling Agent No. 5

A reaction and mixing was carried out under the same conditions as in Synthesis Example 2, but using 0.54 g (2.79 mmol) of 28 wt. % aqueous solution of sodium methoxide (NaOCH$_3$) in place of 20 wt. % aqueous solution of sodium hydroxide, and a white solid substance (e.g. Gelling agent No. 5) of an organically-modified methylpolysiloxane represented by the formula given as below was obtained.

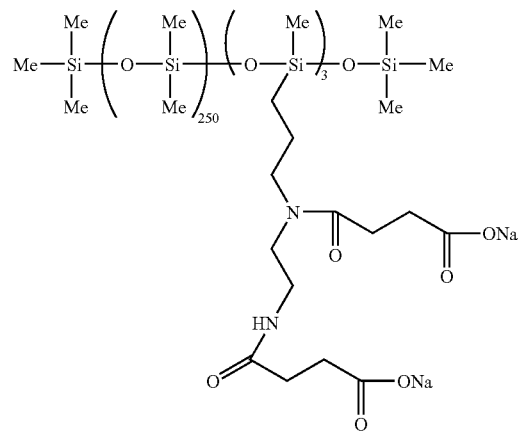

Synthesis Example 6

Gelling Agent No. 6

A reaction and mixing was carried out under the same conditions as in Synthesis Example 2, but using 0.50 g (2.51 mmol, mole number of 90 wt. % with respect to neutralize of terminal carboxylic group) of 20 wt. % aqueous solution of sodium hydroxide in place of 0.56 g (2.79 mmol) of 20 wt. % aqueous solution of sodium hydroxide, a white solid substance (e.g. Gelling agent No. 6) as a mixture of organically-modified methylpolysiloxanes represented by the average structural formulae (i) to (iv) given as below was obtained.

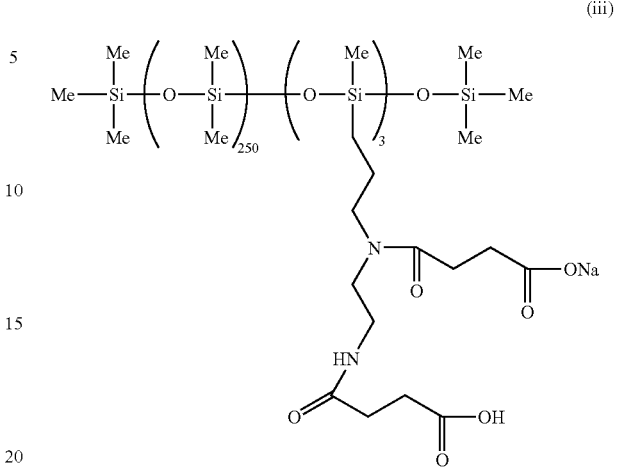

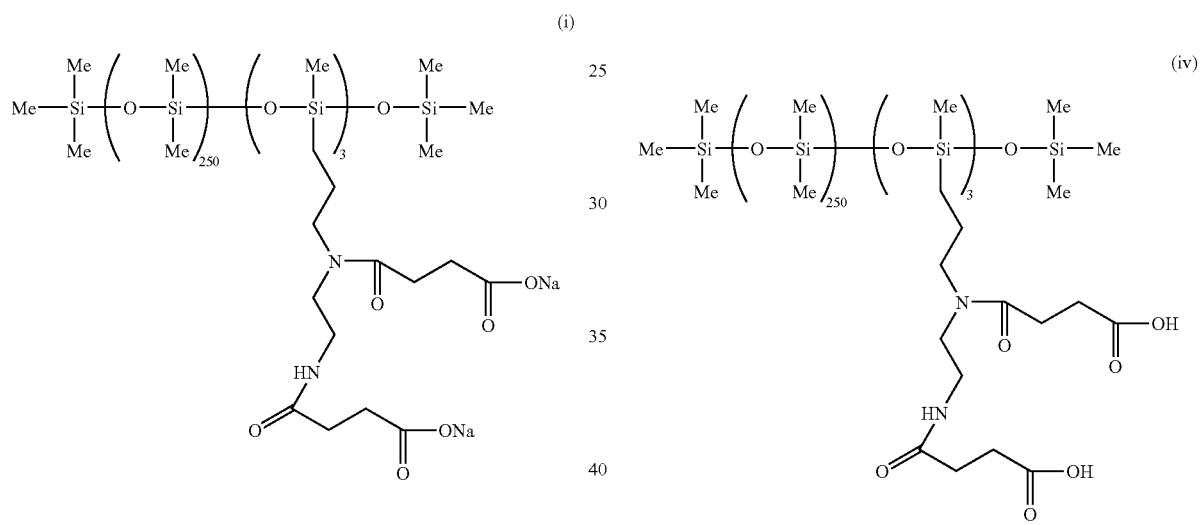

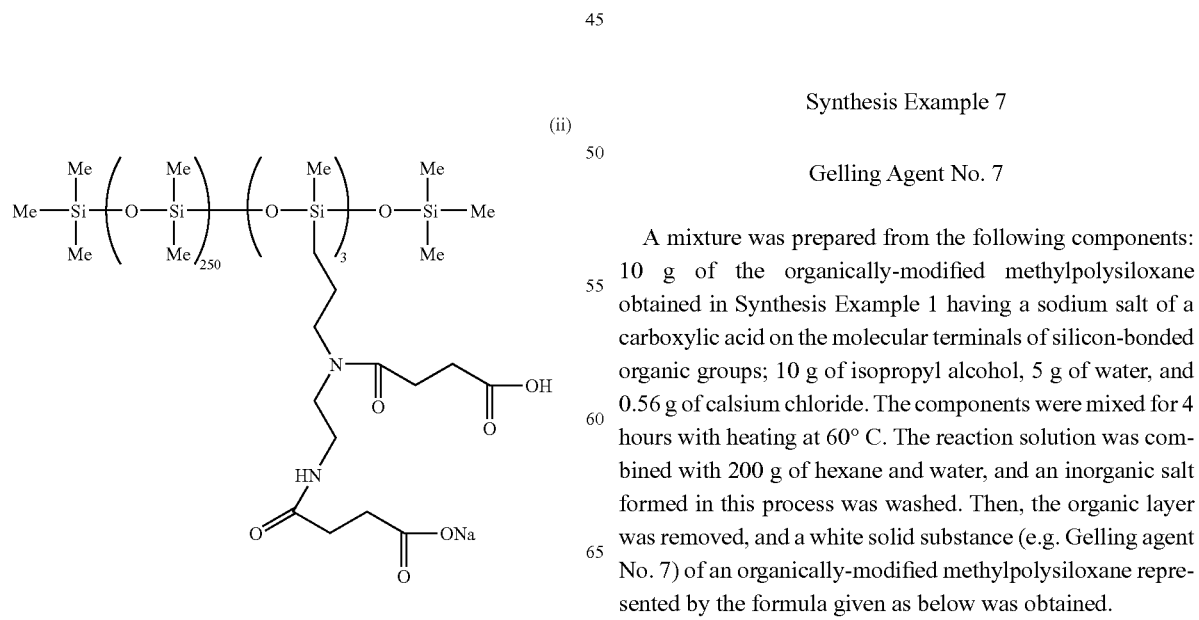

Synthesis Example 7

Gelling Agent No. 7

A mixture was prepared from the following components: 10 g of the organically-modified methylpolysiloxane obtained in Synthesis Example 1 having a sodium salt of a carboxylic acid on the molecular terminals of silicon-bonded organic groups; 10 g of isopropyl alcohol, 5 g of water, and 0.56 g of calsium chloride. The components were mixed for 4 hours with heating at 60° C. The reaction solution was combined with 200 g of hexane and water, and an inorganic salt formed in this process was washed. Then, the organic layer was removed, and a white solid substance (e.g. Gelling agent No. 7) of an organically-modified methylpolysiloxane represented by the formula given as below was obtained.

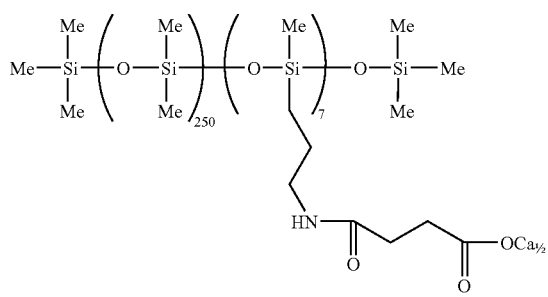

Synthesis Example 8

Gelling Agent No. 8 (for Comparative Example)

A mixture was prepared from 10 g (2.82 mmol of $NH_2$ groups) of a copolymer of a methyl (3-2-aminoethyl aminopropyl) siloxane and dimethylpolysiloxane represented by the following average structural formula:

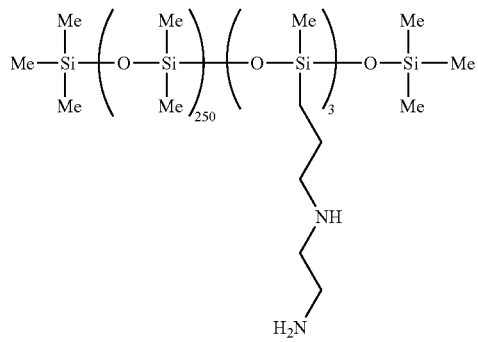

and 0.28 g (2.82 mmol) of an anhydrous succinic acid, which were both mixed in 5 g of ethanol. The mixture was stirred for 5 hr at 30 to 35° C. Results of infrared (IR) analysis showed that specific absorption of carboxylic anhydride was lost, and that specific absorption of amide groups and carboxylic groups was detected. After removal of the ethanol by distillation under reduced pressure, a liquid of low viscosity was obtained. This liquid compound (e.g. Gelling agent No. 8) is comprised of an organically-modified methylpolysiloxane represented by the following average structural formula:

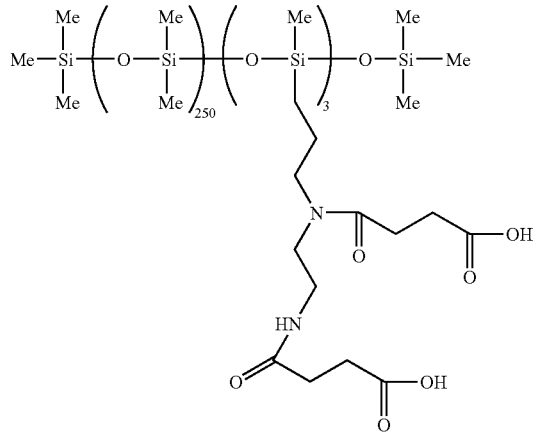

Synthesis Example 9

Gelling Agent No. 9 (for Comparative Example)

A mixture was prepared from 5 g (2.52 mmol of NH2 groups) of a copolymer of methyl (3-aminopropyl) siloxane and dimethylpolysiloxane represented by the following average structural formula:

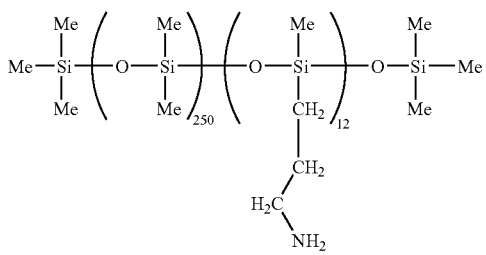

and 0.25 g (2.52 mmol) of an anhydrous succinic acid, which were both mixed in 5 g of ethanol. The mixture was stirred for 5 hr at 30 to 35° C. Results of infrared (IR) analysis showed that specific absorption of carboxylic anhydride was lost, and that specific absorption of amide groups and carboxylic groups was detected. The obtained reaction product was further combined with 0.15 g (2.52 mmol) of 2-aminoalcohol, and a reaction was carried out for 1.0 Hr. at 70° C. Following this, ethanol was removed by distillation with heating in vacuum. As a result, a white solid substance (e.g. Gelling agent No. 9) was obtained. IR analysis showed that the obtained white solid substance was comprised of organically-modified methylpolysiloxane having carboxylic acid (2-amino alcohol) salts on terminals of a silicon-bonded organic group and represented by the following formula:

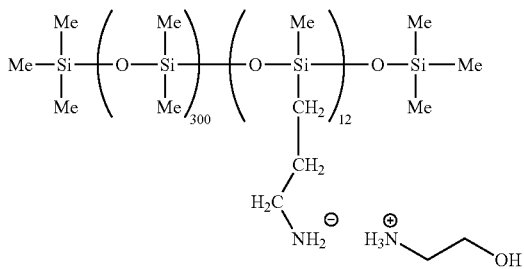

Synthesis Example 10

Gelling Agent No. 10 (for Comparative Example)

A mixture was prepared from 10 g (2.82 mmol of $NH_2$ groups) of a copolymer of a methyl (3-2-aminoethyl aminopropyl) siloxane and dimethylpolysiloxane represented by the following average structural formula:

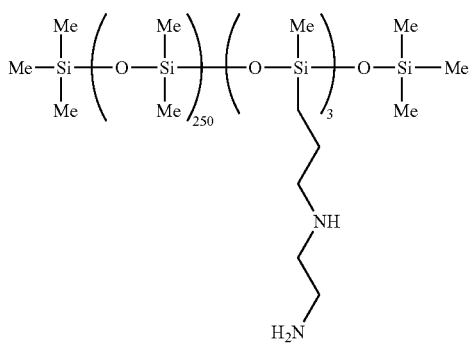

and 0.28 g (2.82 mmol) of an anhydrous succinic acid, which were both mixed in 5.0 g of ethanol. The mixture was stirred for 5 hr at 30 to 35° C. Results of infrared (IR) analysis showed that specific absorption of carboxylic anhydride was lost, and that specific absorption of amide groups and carboxylic groups was detected. The obtained reaction product was further combined with 0.17 g (1.57 mmol) of 2-amino-2-methyl-1,3-propanediol, and a reaction was carried out for 1.0 Hr. at 70° C. Following this, hexane was introduced and the solution was mixed uniformly. And, volatile contents were removed by distillation with heating in vacuum. As a result, a white solid substance (e.g. Gelling agent No. 10) was obtained. IR analysis showed that the obtained white solid substance was a organically-modified methylpolysiloxane represented by the following formula:

infrared (IR) analysis showed that the obtained reaction product was an organically-modified methylpolysiloxane represented by the following formula:

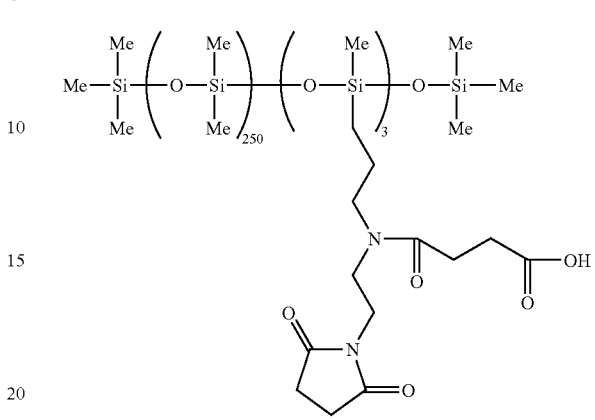

The reaction product was further combined with 20 wt. % aqueous solution of sodium hydroxide, and a reaction was carried out for 30 min at room temperature. Following this, hexane was introduced and the solution was mixed uniformly. And, volatile contents were removed by distillation with heating in vacuum. As a result, a white solid substance (e.g. Gelling agent No. 11) was obtained. IR analysis showed that the obtained white solid substance was an organically-modified methylpolysiloxane represented by the following formula:

Synthesis Example 11

Gelling Agent No. 11 (for Comparative Example)

By mechanically mixing 20 g of the liquid compound obtained in synthesis example 8, an intramolecular condensation reaction was carried out for 3.0 Hr at 110° C. Results of Synthesis Example 12

Gelling Agent No. 12

A mixture was prepared from 30 g (10.2 mmol of NH2 groups) of a copolymer of methyl (3-aminopropyl) siloxane and dimethylpolysiloxane represented by the following average structural formula:

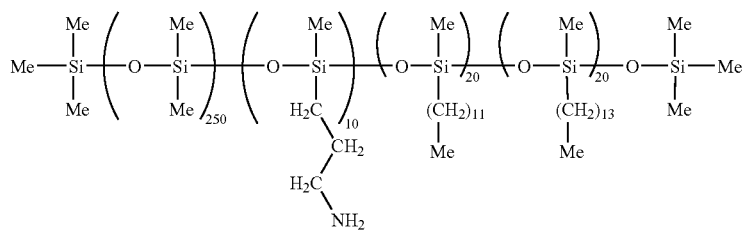

and 1.01 g (10.2 mmol) of an anhydrous succinic acid, which were both mixed in 36 g of isopropyl alcohol. The mixture was stirred for 5 hr at 30 to 35° C. Results of infrared (IR) analysis showed that specific absorption of carboxylic anhydride was lost, and that specific absorption of amide groups and carboxylic groups was detected. This confirmed that the obtained product was comprised of an modified methylpolysiloxane of the following average structural formula:

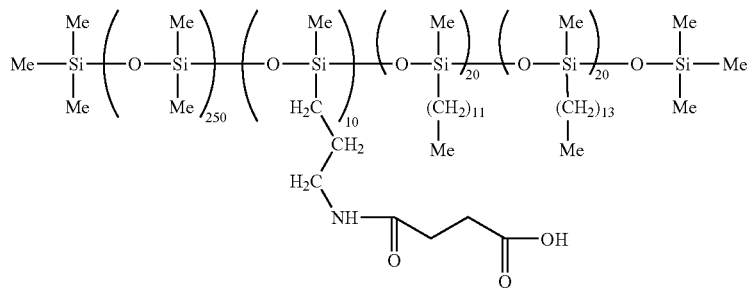

The obtained reaction product was further combined with 2.02 g (10.1 mmol) of 20 wt. % aqueous solution of sodium hydroxide, and a reaction was carried out for 30 min at 25° C. Following this, hexane was introduced and the solution was mixed uniformly. And, volatile contents were removed by distillation with heating in vacuum. As a result, a white solid substance (e.g. Gelling agent No. 12) was obtained. IR analysis showed that the obtained white solid substance was comprised of organically-modified methylpolysiloxane having carboxylic acid sodium salts on terminals of a silicon-bonded organic group and represented by the following formula:

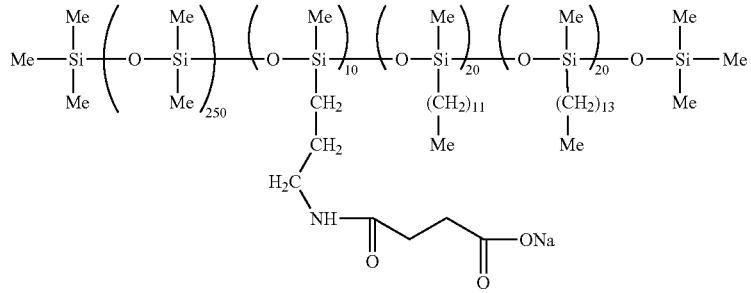

Synthesis Example 13

Gelling Agent No. 13

A mixture was prepared from 30 g (10.0 mmol of $NH_2$ groups) of a copolymer of a methyl (3-2-aminoethyl aminopropyl) siloxane and dimethylpolysiloxane represented by the following average structural formula:

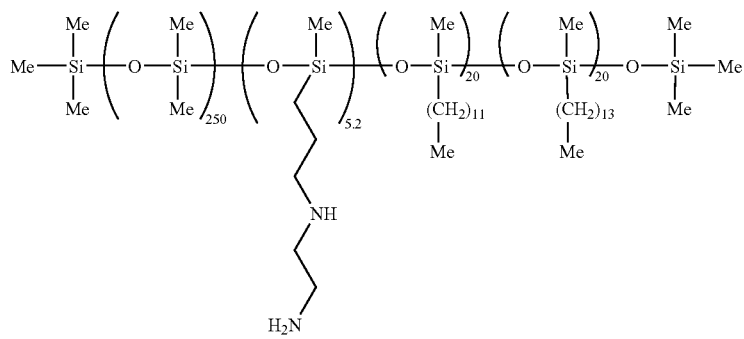

and 1.0 g (10.0 mmol) of an anhydrous succinic acid, which were both mixed in 36 g of isopropyl alcohol. The mixture was stirred for 5 hr at 30 to 40° C. Results of infrared (IR) analysis showed that specific absorption of carboxylic anhydride was lost, and that specific absorption of amide groups and carboxylic groups was detected. The obtained reaction product was cooled to the room temperature and further combined with 1.98 g (9.9 mmol) of a 20 wt. % aqueous solution of sodium hydroxide, and a reaction was carried out for 30 min. at room temperature. Following this, hexane was introduced and the solution was mixed uniformly. And, volatile contents were removed by distillation with heating in vacuum. As a result, a white solid substance (e.g. Gelling agent No. 13) was obtained. IR analysis showed that the obtained white solid substance was comprised of organically-modified methylpolysiloxane having carboxylic acid sodium salts on terminals of a silicon-bonded organic group and represented by the following formula:

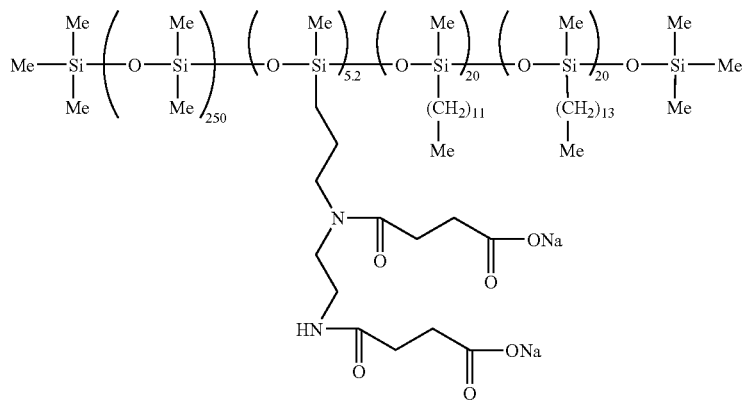

Synthesis Example 14

Gelling Agent No. 14

A reaction and mixing was carried out under the same conditions as in Synthesis Example 13, but using 2.78 g (9.9 mmol) of 20 wt. % aqueous solution of potassium hydroxide in place of 20 wt. % aqueous solution of sodium hydroxide, and a white solid substance (e.g. Gelling agent No. 14) of an organically-modified methylpolysiloxane represented by the formula given below was obtained.

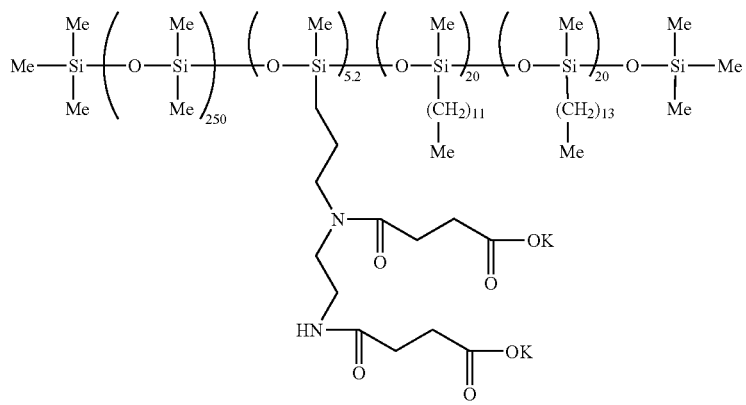

Synthesis Example 15

Gelling Agent No. 15

A mixture was prepared from 30 g (9.5 mmol of NH2 groups) of a copolymer of methyl (3-aminopropyl) siloxane and dimethylpolysiloxane represented by the following average structural formula:

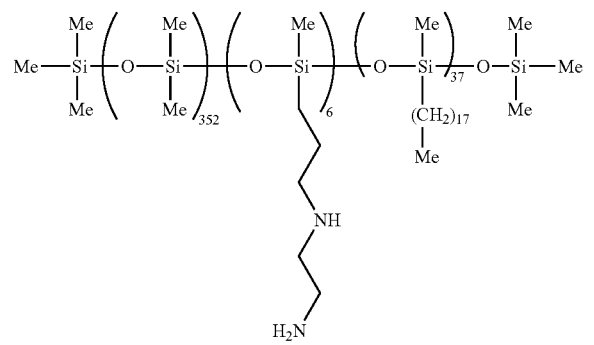

and 1.01 g (10.2 mmol) of an anhydrous succinic acid, which were both mixed in 36 g of isopropyl alcohol. The mixture was stirred for 5 hr at 30 to 40° C. Results of infrared (IR) analysis showed that specific absorption of carboxylic anhydride was lost, and that specific absorption of amide groups and carboxylic groups was detected. Then, the obtained reaction product was further combined with 2.02 g (10.1 mmol) of a 20 wt. % aqueous solution of sodium hydroxide, and a reaction was carried out for 30 min at room temperature. Following this, hexane was introduced and the solution was mixed uniformly. And, volatile contents were removed by distillation with heating in vacuum. As a result, a white solid substance (e.g. Gelling agent No. 15) was obtained. IR analysis showed that the obtained white solid substance was comprised of organically-modified methylpolysiloxane having carboxylic acid sodium salts on terminals of a silicon-bonded organic group and represented by the following formula:

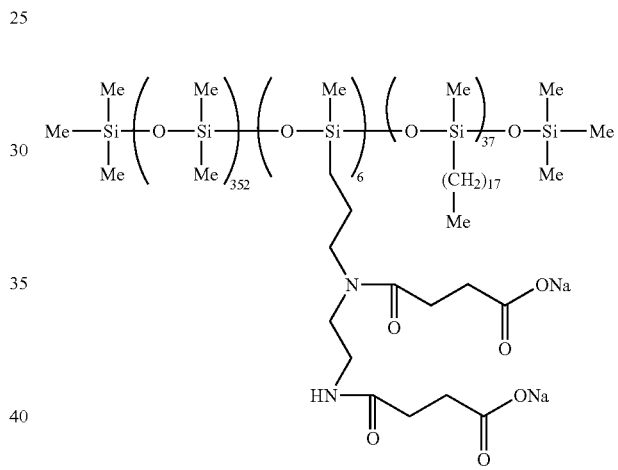

Synthesis Example 16

Gelling Agent No. 16

A mixture was prepared from the following components: 10 g of the organically-modified methylpolysiloxane obtained in Synthesis Example 12 having a sodium salt of a carboxylic acid on the molecular terminals of silicon-bonded organic groups; 10 g of isopropyl alcohol, 5 g of water, and 0.56 g of calsium chloride. The components were mixed for 4 hours with heating at 60° C. The reaction solution was combined with 200 g of hexane and water, and an inorganic salt formed in this process was washed. Then, the organic layer was removed, and a white solid substance (e.g. Gelling agent No. 16) of an organically-modified methylpolysiloxane represented by the formula given as below was obtained.

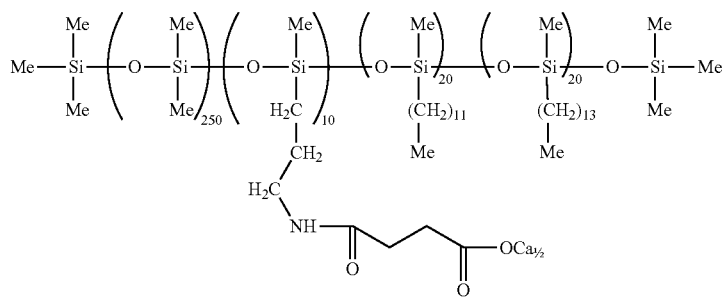

Reference Example 1

The gel-forming ability of the organically-modified methylpolysiloxanes obtained in Synthesis Examples 1 to 16 (e.g. Gelling agent No. 1 to 16) was evaluated by using the evaluation method and assessment criteria shown as below, and the results are shown in Table 1. The designation "No. X" in the gelling agent column represents an organically-modified methylpolysiloxane obtained in a Synthesis Example X.

[Method of Evaluation]

A mixture consisting of 7.5 wt % of gelling agent and 92.5 wt % of decamethylpentasiloxane was stirred under heating at 80° C. or 110° C. for 2 hours and then cooled to room temperature.

[Evaluation Criteria]

○: A highly thixotropic gel is formed.

Δ: A viscous liquid is formed.

x: Liquid (no gelling).

TABLE 1

| Ingredient (a): | Ingredient (b): decamethylpentasiloxane (92.5 wt %) | |
|---|---|---|
| Gelling agent (7.5 wt %) | Stirring at 80° C. | Stirring at 110° C. |
| No. 1 | ○ | ○ |
| No. 2 | ○ | ○ |
| No. 3 | ○ | ○ |
| No. 4 | Δ | Δ |
| No. 5 | ○ | ○ |
| No. 6 | ○ | ○ |
| No. 7 | ○ | ○ |
| No. 8 | X | X |
| No. 9 | ○ | X |
| No. 10 | ○ | X |
| No. 11 | X | X |
| No. 12 | ○ | ○ |
| No. 13 | ○ | ○ |
| No. 14 | ○ | ○ |
| No. 15 | ○ | ○ |
| No. 16 | ○ | ○ |

As can be seen from the results listed in Table 1, the organopolysiloxanes having organic groups represented by the general formula (1), i.e. the gelling agents obtained in Synthesis Examples 1 to 3, 5 to 7 and 12 to 16, were capable of efficiently gelling silicone oils at a high temperature of 110° C. even when a small amount was added. The gelling agent No. 4 formed a viscous liquid under the above condition, but when the amount exceeded 20 wt %, it was able to gel decamethylpentasiloxane. On the other hand, when the organically-modified organopolysiloxanes of Synthesis Examples 8 through 11 were subjected to stirring under heating at a high temperature of 110° C., they were unable to form a gelatinous composition. For this, their heat resistance was inferior to that of the above-mentioned gelling agents of the present invention.

Reference Example 2

A mixture was prepared from 7.5 wt % of a gelling agent obtained in aforementioned Synthesis Example 2 (e.g. Gelling agent No. 2), 60.5 wt % of decamethylpentacyclosiloxane and 32 wt % of cosmetic oil compounds given in the below table (Additional decamethylpentacyclosiloxane, Isononyl isononanoate, Squalane, Liquid paraffin and Phenyltrimethicone). After these components were stirred for 2 Hr at 80° C., and the mixed solution was cooled to obtain gelatinous composition. As a result, the appearance and refractive index of gelatinous compositions was shown in below Table 2.

TABLE 2

| Re. Ex. | Gelling agent | cosmetic oil compounds | appearance | refractive index |
|---|---|---|---|---|
| 2-1 | No. 2 | decamethylpentacyclosiloxane *1 | transparent gel | 1.3980 |
| 2-2 | No. 2 | Isononyl isononanoate | transparent gel | 1.4115 |
| 2-3 | No. 2 | Squalane | transparent gel | 1.4213 |
| 2-4 | No. 2 | Liquid paraffin | transparent gel | 1.4192 |
| 2-5 | No. 2 | Phenyltrimethicone *2 | transparent gel | 1.4188 |

*1: Sample gelled with only 92.5 wt % decamethylpentasiloxane
*2: SH556 from Dow Corning Toray Co., Ltd. was used as the phenyltrimethicone

Reference Example 3

A mixture was prepared from 7.5 wt % of a gelling agent obtained in aforementioned Synthesis Example 15 (e.g. Gelling agent No. 15), 60.5 wt % of decamethylpentacyclosiloxane and cosmetic oil compounds given in the below table (paraffin wax, tri caprylic/capric glyceride ester, trioctanoine, phenyltrimethicone, and scwaran). After these components were stirred for 2 Hr at 80° C., and the mixed solution was cooled to obtain gelatinous composition. As a result, the appearance and refractive index of gelatinous compositions were shown in below Table 3.

TABLE 3

| Re. Ex. | Gelling agent | cosmetic oil compounds | appearance | refractive index |
|---|---|---|---|---|
| 3-1 | No. 15 | Paraffin wax | transparent gel | 1.4237 |
| 3-2 | No. 15 | Tri caprylic/capric glyceride ester | transparent gel | 1.4171 |
| 3-3 | No. 15 | Trioctanoine | transparent gel | 1.4153 |

TABLE 3-continued

| Re. Ex. | Gelling agent | cosmetic oil compounds | appearance | refractive index |
|---|---|---|---|---|
| 3-4 | No. 15 | Phenyltrimethicone | transparent gel | 1.4179 |
| 3-5 | No. 15 | Squalane | transparent gel | 1.4196 |

As can be seen from Table 2 and Table 3, when the gelling agent was an organopolysiloxane having organic groups represented by the general formula (1), it was possible to form gelatinous compositions using representative non-polar organic compounds or low-polarity organic compounds added to cosmetic products and the appearance of these gel compositions was sufficiently transparent.

Reference Example 4

The gelling agent No. 2 was subjected to testing to determine their moisture retention properties. In similar manner, for the comparative example, a side chain polyoxyethylene-modified polydimethylsiloxane (polyoxyethylene group content: 64 wt %) as well as glycerin were subjected to testing to determine their moisture retention properties. The method used for testing was as shown below. The results are shown in FIG. 1.

[Method of Evaluation]

A 1 g of sample was placed in a flat-bottomed aluminum container with a diameter of 60 mm and dried at 105° C. for 3 hours. Then, the sample was allowed to stand for 40 hours in a high-humidity thermostat at 60° C./90% RH, and the mass of the sample that had absorbed sufficient moisture was accurately weighed. The sample was allowed to stand at 20° C./70% RH, and its mass was accurately weighed at regular intervals to obtain the amount of evaporated moisture.

As can be seen from FIG. 1, the rate of moisture evaporation from the gelling agent No. 2 was 1/4 of the rate of the side chain polyoxyethylene-modified polydimethylsiloxane, and 1/8 of the rate of the glycerin used for the comparative examples. Based on this, it was evident that the gelling agent of this invention was useful for retaining skin or hair moisture.

Reference Example 5

The aforementioned gelling agent No. 7, which was an organically-modified methylpolysiloxane containing a calcium salt of a carboxylic acid was subjected to testing to determine its curl retention to human hair. In similar manner, for the comparative example, a cross-linkable silicone elastomer (called dimethicone crosspolymer in the nomenclature of cosmetic ingredients) or a silicone resin (called trimethylsiloxysilicate) were subjected to testing to determine their curl retention to human hair. The method used for testing was as shown below. The results are shown in FIG. 2.

[Method of Evaluation]

Test specimens were obtained by cleansing a bundle of untreated hair from an Asian person with a length of about 27 cm and a weight of about 2 g using a shampoo that did not contain silicones and rinsed, removing water with a towel and allowing it to dry naturally overnight in a suspended state at room temperature.

The test specimens were immersed and soaked in samples dissolved in hexamethyldisiloxane to produce a 2 wt % concentration of the active ingredient, with the excess solution removed with fingers. The test specimens were wrapped around glass tubes with a diameter of 15 mm without gaps, with the ends secured using clips. The specimens were dried for 30 minutes in a vertical position in an oven at 105° C. The specimens were then removed from the glass tubes and allowed to cure at laboratory conditions (22° C./60% RH) in a suspended state, whereupon the length of the bundle between the upper and lower ends thereof was measured (initial length of curl L(0)). The specimens were suspended in a high-humidity thermostat at 30° C./80%/RH and the length of the specimens was measured at certain points in time (t) (curl length L(t)).

Curl retention was calculated as value obtained using the formula.

Curl retention (%)={(27−L(t))/(27−L(0))}×100

As can be seen from FIG. 2, it is revealed that the curl retention provided by using the gelling agent of this invention was superior to that of the blank, the cross-linkable silicone elastomer or the silicone resin.

Practical Examples

Cosmetics

If not specified otherwise, the term "gelling agent (Synthesis Example X)" used in the practical examples shown below refers to the organically-modified methylpolysiloxane illustrated in the above-mentioned Synthesis Example X. In addition, the symbol "%" refers to weight percent.

Practical Example 1

Sunscreen Gel

| (Ingredients) | (wt %) |
|---|---|
| 1. Gelling agent (Synthesis Example 2) | 6.0 |
| 2. Methyltrimethicone *1 | 85.5 |
| 3. Phenyltrimethicone *2 | 6.0 |
| 4. Ethylhexyl methoxycinnamate | 2.0 |
| 5. Fragrance | Suitable amount |

*1: Methyltrimethicone represents methyltristrimethylsiloxysilane.
*2: SH556 from Dow Corning Toray Co., Ltd. was used as the phenyltrimethicone.

(Method of Preparation)

Ingredients 1-4 were heated to 90° C. and uniformly dissolved in a dispersing machine. The dissolved viscous liquid was cooled to 50° C., after which ingredient 5 was added to the liquid, producing a sunscreen gel.

The sunscreen gel of Practical Example 1 had a rich, superior "as-applied" feel, and had superior UV light protective effects. In addition, the temporal stability of the formulation was superior. The gel exhibited superior transparency and stability, spread smoothly to produce an excellent sensory feel, had a superior in-use sensory feel, and did not sag.

Practical Example 2

Sunscreen Cream

| (Ingredients) | (wt %) |
|---|---|
| 1. Gelling agent (Synthesis Example 6) | 5.0 |
| 2. Decamethylpentasiloxane | 25.0 |

-continued

| (Ingredients) | (wt %) |
| --- | --- |
| 3. Dimethylpolysiloxane (6 mPas) | 3.0 |
| 4. Trimethylsiloxysilicic acid | 3.0 |
| 5. Polyoxyethylene-methylpolysiloxane copolymer | 3.0 |
| 6. 2-Ethylhexyl myrystate | 2.0 |
| 7. Spherical organopolysiloxane elastomer powder *2 | 2.0 |
| 8. Silicone-treated superfine titanium oxide particulate | 10.0 |
| 9. Silicone-treated superfine zinc oxide particulate | 10.0 |
| 10. Talc | 2.0 |
| 11. Dipropylene glycol | 2.0 |
| 12. Purified water | Remainder |
| 13. Paraben | Suitable amount |
| 14. Phenoxyethanol | Suitable amount |

*1: SH3772c from Dow Corning Toray Co., Ltd. was used as the polyoxyethylene-methylpolysiloxane copolymer.
*2: Trefil E-508 from Dow Corning Toray Co., Ltd. was used as the spherical organopolysiloxane elastomer powder.

(Method of Preparation)

A: Ingredients 1-7 were stirred under heating at 90° C. in a dispersing machine.

B: Ingredients 8-10 were added to the solution prepared in A and stirred in the dispersing machine.

C: Ingredients 11, 12 were slowly added to the solution prepared in B and emulsified.

D: Ingredients 13, 14 were added to C, producing a sunscreen cream.

Evaluation of the in-use sensory feel of the sunscreen cream of Practical Example 2 revealed that because the oil phase of the cream had been stabilized by the product of the present invention, the cream exhibited superior temporal stability, had a smooth "as-applied" feel, and exhibited excellent UV light protective properties and resistance to skin oils.

Practical Example 3

Sunscreen Emulsion

| (Ingredients) | (wt %) |
| --- | --- |
| 1. Gelling agent (Synthesis Example 5) | 2.0 |
| 2. Trioctanoin | 10.0 |
| 3. Decamethylpentasiloxane | 20.0 |
| 4. Cross-linkable polyether-modified silicone*1 | 5.0 |
| 5. Silicone-treated superfine titanium oxide particulate | 10.0 |
| 6. Silicone-treated superfine zinc oxide particulate | 10.0 |
| 7. Ion exchange water | 45.0 |
| 8. Dipropylene glycol | 3.0 |
| 9. 1,3-butyleneglycol | 3.0 |
| 10. Paraben | Suitable amount |

*1DC9011 from Dow Corning Toray Co., Ltd. was used as the cross-linkable polyether-modified silicone.

(Method of Preparation)

A: Ingredients 1-4 were stirred under heating at 90° C. in a dispersing machine.

B: Ingredients 5-6 were added to the solution prepared in A and stirred in the dispersing machine.

C: Ingredients 7, 9 were slowly added to the solution prepared in B and emulsified, whereupon ingredient 10 was added to yield a sunscreen emulsion.

Evaluation of the in-use sensory feel of the sunscreen emulsion of Practical Example 3 revealed that because the oil phase had been stabilized by the product of the present invention, no separation took place, and the emulsion exhibits superior adhesion to the skin. The emulsion had the ability to improve makeup hold when used in foundations.

Practical Example 4

Oily Foundation

| (Ingredients) | (wt %) |
| --- | --- |
| 1. Gelling agent (Synthesis Example 2) | 5.0 |
| 2. Carbosiloxane dendrimer graft type acrylic copolymer | 2.0 |
| 3. Decamethylpentacyclosiloxane | Remainder |
| 4. Octyl para-methoxycinnamate | 4.0 |
| 5. Dimethylpolysiloxane (6 mPa-s) | 3.0 |
| 6. Methyltrimethicone*1 | 15.0 |
| 7. Phenyltrimethicone*2 | 1.0 |
| 8. Cross-linkable polyether-modified silicone*3 | 5.0 |
| 9. Alkylsilane-treated titanium oxide | 10.0 |
| 10. Alkylsilane-treated zinc oxide | 15.0 |

*1Methyltristrimethylsiloxysilane was used as the methyltrimethicone.
*2SH556 from Dow Corning Toray Co., Ltd. was used as the phenyltrimethicone.
*3DC9011 from Dow Corning Toray Co., Ltd. was used as the cross-linkable polyether-modified silicone.

(Method of Preparation)

A: Ingredients 1-8 were stirred under heating at 90° C. in a dispersing machine.

B: Ingredients 9 through 10 were stirred in a dispersing machine.

C: B was slowly added while stirring A in a dispersing machine, yielding an oily foundation.

Evaluation of the in-use sensory feel of the oily foundation of Practical Example 4 revealed that the oily foundation had superior makeup-holding properties, did not sag, and produced a superior in-use sensory feel.

Practical Example 5

Emulsified Foundation (O/W Type)

| (Ingredients) | (wt %) |
| --- | --- |
| 1. Gelling agent (Synthesis Example 7) | 2.0 |
| 2. Squalane | 2.0 |
| 3. 2-Ethylhexyl myrystate | 5.0 |
| 4. Dimethylpolysiloxane (6 mPa-s) | 2.0 |
| 5. Decamethylpentasiloxane | 10.0 |
| 6. Polyoxyethylene-methylpolysiloxane copolymer | 5.0 |
| 7. Glycerin | 3.0 |
| 8. Ethanol | 2.0 |
| 9. Ion exchange water | Remainder |
| 10. Antiseptic agent | Suitable amount |

*1SH3772c was used as the polyoxyethylene-methylpolysiloxane copolymer.

(Method of Preparation)

A: Ingredients 1-6 were stirred under heating at 80° C. in a dispersing machine.

B: Ingredients 7-10 were added to the solution prepared in A and emulsified in the dispersing machine, yielding an emulsified foundation (O/W type).

Evaluation of the in-use sensory feel of the emulsified foundation (O/W type) of Practical Example 5 revealed that the use of the gelling agent (Synthesis Example 7) improved the stability of the oily phase and produced a foundation with a refreshing feel.

Practical Example 6

Emulsified Foundation (W/O Type)

| (Ingredients) | (wt %) |
|---|---|
| 1. Gelling agent (Synthesis Example 2) | 3.0 |
| 2. Decamethylpentacyclosiloxane | 8.0 |
| 3. Diisostearyl maleate | 9.0 |
| 4. Liquid paraffin | 5.0 |
| 5. Isononyl isononanoate | 5.0 |
| 6. Dimethylpolysiloxane (6 mPa-s) | 3.0 |
| 7. Dimethylsiloxane-methylpolyoxyethylenesiloxane copolymer*1 | 5.0 |
| 8. Spherical organopolysiloxane elastomer powder*2 | 2.0 |
| 9. Silicone-treated titanium oxide microparticulate | 5.0 |
| 10. Silicone-treated zinc oxide microparticulate | 5.0 |
| 11. Silicone-treated iron oxide microparticulate | 5.0 |
| 12. 1,3-butyleneglycol | 3.0 |
| 13. Ion exchange water | Remainder |
| 14. Antiseptic agent | Suitable amount |
| 15. Fragrance | Suitable amount |

*1SH3775c from Dow Corning Toray Co., Ltd. was used as the dimethylsiloxane-methylpolyoxyethylenesiloxane copolymer.
*2Trefil E-508 from Dow Corning Toray Co., Ltd. was used as the spherical organopolysiloxane elastomer powder.

(Method of Preparation)
A: Ingredients 1-7 were heated to 80° C. and uniformly dispersed.
B: Ingredients 8-11 were added to A and uniformly dispersed.
C: Ingredients 12-14 were uniformly mixed.
D: C was added to B at 50° C. and the mixture was emulsified.
E: Upon cooling, ingredient 15 was added and mixed with D, yielding an emulsified foundation (W/O type).

Evaluation of the in-use sensory feel of the emulsified foundation (W/O type) of Practical Example 6 revealed that the emulsified (W/O type) foundation prepared in accordance with this recipe exhibited superior makeup holding properties and wrinkle-hiding effects, a smooth "as-applied" feel, good affinity to the skin and excellent stability.

Practical Example 7

Curl Retaining Agent for Hair

| (Ingredients) | (wt %) |
|---|---|
| 1. Gelling agent (Synthesis Example 7) | 2.0 |
| 2. Decamethylpentacyclosiloxane | 6.0 |
| 3. Methylphenylpolysiloxane | 1.0 |
| 4. Highly polymerized silicone decamethylpentasiloxane solution | 1.0 |
| 5. 2-Ethylhexyl myrystate | 1.0 |
| 6. Sorbitan monoisostearate | 2.0 |
| 7. Squalane | 1.0 |
| 8. Purified water | Remainder |
| 9. 1,3-butyleneglycol | 1.0 |
| 10. Antiseptic agent | Suitable amount |

(Method of Preparation)
A: Ingredients 1-7 were mixed under heating at 80° C.
B: Ingredients 8-10 were uniformly mixed.
C: B was slowly added to A, the mixture was emulsified and then subjected to treatment in a homogenizer, yielding a curl-retaining agent for hair.

Evaluation of the in-use feel of the curl-retaining agent of Practical Example 7 revealed that, due to the effects produced by the present gelling agent, the curl-retaining agent for hair prepared using the present composition had superior glossiness, setting properties, durability, and stability.

Practical Example 8

Oil Cleansing Gel (Rinse-Off Type)

| (Composition) | (%) |
|---|---|
| 1. Gelling agent (Synthesis Example 2) | 6.0 |
| 2. Liquid paraffin | 30.0 |
| 3. Decamethylpentasiloxane | 56.0 |
| 4. Polyoxyethylene-methylpolysiloxane copolymer | 5.0 |
| 5. Propylene glycol | 3.0 |

*1SH3772c from Dow Corning Toray Co., Ltd. was used as the dimethylsiloxane-methylpolyoxyethylenesiloxane copolymer.

(Method of Preparation)
Ingredients 1-5 were uniformly mixed at 80° C., producing a cleansing gel.
(Method of Evaluation)
Commercially available skin oil-resistant foundation and long-lasting type lipstick were applied to the skin, after which an appropriate amount of the oil cleansing gel of Practical Example 8 was applied to the coating film, rubbed in with fingers to mix it with the film, washed off with water and then cleaned with soap.
(Evaluation Results)
The foundation and lipstick applied to the skin were completely washed off using the cleansing gel, which showed that the gel had superior cleansing power. In addition, the sensory feel produced by the gel was the unique light sensory feel characteristic of silicone oils, and its in-use sensory feel was superior as well.

Practical Example 9

Oil Cleansing Gel (Wipe-Off Type)

| (Composition) | (wt %) |
|---|---|
| 1. Gelling agent (Synthesis Example 2) | 6.0 |
| 2. Isononyl isononanoate | 32.0 |
| 3. Decamethylpentasiloxane | 59.0 |
| 4. Propylene glycol | 3.0 |

(Method of Preparation)
Ingredients 1-5 were uniformly mixed at 80° C., producing a cleansing gel.
(Method of Evaluation)
Commercially available skin oil-resistant foundation and long-lasting type lipstick were applied to the skin, after which an appropriate amount of the oil cleansing gel of Practical Example 9 was applied to the coating film, rubbed in with fingers to mix it with the film, and then wiped off with a cotton ball. In addition, a cleansing agent, which had been prepared in the same manner as in Practical Example 9, with the exception of using decamethylpentasiloxane instead of the gelling agent, was subjected to evaluation in the same manner.
(Evaluation Results)
The skin oil resistant oily foundation and lipstick applied to the skin were completely wiped off when the cleansing gel was used, which showed that the gel had superior cleansing power. In addition, the sensory feel produced by the gel was the unique light sensory feel characteristic of silicone oils, its in-use sensory feel was excellent, and the gel also had superior transparency. On the other hand, when the gelling agent was not used, traces of residual skin oil-resistant oily foundation were produced, and the cleansing performance was insufficient. In addition, when the gelling agent of the present invention was not used, the viscosity of the gel was low, causing it to run, and its in-use sensory feel was poor as well.

Practical Example 10

Lipstick

| (Ingredients) | (wt %) |
|---|---|
| 1. Gelling agent (Synthesis Example 2) | 8.0 |
| 2. Squalane | 6.0 |
| 3. Dimethylpolysiloxane (6 mPa-s) | 5.0 |
| 4. Decamethylpentasiloxane | 50.0 |
| 5. Polyoxyethylene-methylpolysiloxane copolymer*1 | 3.0 |
| 6. Trimethylsiloxysilicic acid | 8.0 |
| 7. Alkyl modified polysiloxane*2 | 3.0 |
| 8. Methylphenylpolysiloxane | 5.0 |
| 9. Silicone-treated pigment | Suitable amount |
| 10. Dye | Suitable amount |
| 11. Synthetic sodium magnesium silicate | 1.0 |
| 12. Fragrance | Suitable amount |

*1SH3775c from Dow Corning Toray Co., Ltd. was used as the dimethylsiloxane-methylpolyoxyethylenesiloxane copolymer.
*2DC2503 from Dow Corning Toray Co., Ltd. was used as the alkyl modified polysiloxane.

(Method of Preparation)
A: Ingredients 1-8 were uniformly mixed and stirred under heating at 80° C.
C: Ingredients 9-12 were uniformly dispersed.
C: B was slowly added to A, the mixture was packed into a container, yielding a lipstick.

Evaluation of the in-use sensory feel of the lipstick of Practical Example 10 revealed that the lipstick obtained from the above-described composition had the unique silicone-like light sensory feel and at the same time exhibited a smooth "as applied" feel and transparent appearance.

Practical Example 11

Lip Gloss

| (Ingredients) | (wt %) |
|---|---|
| 1. Gelling agent (Synthesis Example 2) | 5.0 |
| 2. Dimethylpolysiloxane (6 mPa-s) | 20.0 |
| 3. Dimethylpolysiloxane (10,000 mPa-s) | Remainder |
| 4. Methylphenylpolysiloxane | 10.0 |
| 5. Pigment | Suitable amount |
| 6. Legally permitted colorant | Suitable amount |

(Method of Preparation)
Ingredients 1-6 were heated and mixed at 80° C., producing a uniform solution, whereupon the mixture was poured into a mold and allowed to cool, solidifying and producing a lip gloss.

Evaluation of the in-use sensory feel of the lip gloss of Practical Example 11 revealed that the lip gloss prepared from the composition exhibited superior spread property and gloss, did not have a sticky feel, and had a superior in-use sensory feel.

Practical Example 12

Sunscreen Emulsion (W/O Type)

| (Ingredients) | (wt %) |
|---|---|
| 1. Gelling agent (Synthesis Example 12) | 5.0 |
| 2. Methyltrimethicone | 25.0 |
| 3. Dimethylpolysiloxane (6 mPa-s) | 3.0 |
| 4. Carbosiloxane dendrimer graft type acrylic copolymers | 3.0 |
| 5. Polyoxyethylene-methylpolysiloxane copolymer*1 | 3.0 |
| 6. Tri caprylic/capric glyceride ester | 3.0 |
| 7. Spherical organopolysiloxane elastomer powder*2 | 2.0 |
| 8. Silicone-treated superfine titanium oxide particulate | 10.0 |
| 9. Silicone-treated superfine zinc oxide particulate | 10.0 |
| 10. Spherical PMMA powder | 2.0 |
| 11. Dipropylene glycol | 2.0 |
| 12. Ion exchange water | Remainder |
| 13. Antiseptic agent | Suitable amount |
| 14. Fragrance | Suitable amount |

*1SH3772C from Dow Corning Toray Co., Ltd. was used as Polyoxyethylene-methylpolysiloxane copolymer
*2Trefil E-508 from Dow Corning Toray Co., Ltd. was used as the spherical organopolysiloxane elastomer powder.

(Method of Preparation)
A: Ingredients 1-7 were stirred under heating at 90° C. in a dispersing machine.
B: Ingredients 8-10 were added to the solution prepared in A and stirred in the dispersing machine.
C: Ingredients 11, 12 were slowly added to the solution prepared in B and emulsified.
D: Ingredients 13, 14 were added to C, producing a Sunscreen emulsion (W/O type).

Evaluation of the in-use sensory feel of the Sunscreen emulsion (W/O type) of Practical Example 12 revealed that because the oil phase of the cream had been stabilized by the product of the present invention, the cream exhibited superior temporal stability, had a smooth "as-applied" feel, and exhibited excellent UV light protective properties and resistance to skin oils.

Practical Example 13

Oily Foundation

| (Ingredients) | (wt %) |
|---|---|
| 1. Gelling agent (Synthesis Example 13) | 5.0 |
| 2. Trimethylsiloxysilicic acid | 2.0 |
| 3. Decamethylpentacyclosiloxane | Remainder |
| 4. Octyl para-methoxycinnamate | 4.0 |
| 5. Methyltrimethicone*1 | 10.0 |
| 6. Tri caprylic/capric glyceride ester | 3.0 |

-continued

| (Ingredients) | (wt %) |
|---|---|
| 7. Caprylicmethicone*2 | 1.0 |
| 8. Cross-linkable polyether-modified silicone*3 | 5.0 |
| 9. Alkylsilane-treated titanium oxide | 10.0 |
| 10. Alkylsilane-treated zinc oxide | 15.0 |

*1Methyltristrimethylsiloxysilane was used as the methyltrimethicone.
*2SS3408 from Dow Corning Toray Co., Ltd. was used as the caprylicmethicone.
*3DC9011 from Dow Corning Toray Co., Ltd. was used as the cross-linkable polyether-modified silicone.

(Method of Preparation)

A: Ingredients 1-8 were stirred under heating at 90° C. in a dispersing machine.

B: Ingredients 9 through 10 were stirred in a dispersing machine.

C: B was slowly added while stirring A in a dispersing machine, yielding an oily foundation.

Evaluation of the in-use sensory feel of the oily foundation of Practical Example 13 revealed that the oily foundation had superior makeup-holding properties, did not sag, and produced a superior in-use sensory feel.

Practical Example 14

Emulsified Foundation (W/O Type)

| (Ingredients) | (wt %) |
|---|---|
| 1. Gelling agent (Synthesis Example 13) | 3.0 |
| 2. Decamethylpentacyclosiloxane | 8.0 |
| 3. hardened castor oil | 9.0 |
| 4. Paraffin wax | 5.0 |
| 5. Isononyl isononanoate | 5.0 |
| 6. Dimethylpolysiloxane (6 mPa·s) | 3.0 |
| 7. Dimethylsiloxane-methylpolyoxyethylenesiloxane copolymer*1 | 5.0 |
| 8. Spherical organopolysiloxane elastomer powder*2 | 2.0 |
| 9. Silicone-treated titanium oxide microparticulate | 5.0 |
| 10. Silicone-treated zinc oxide microparticulate | 5.0 |
| 11. Silicone-treated iron oxide microparticulate | 5.0 |
| 12. 1,3-butyleneglycol | 3.0 |
| 13. Ion exchange water | Remainder |
| 14. Antiseptic agent | Suitable amount |
| 15. Fragrance | Suitable amount |

*1SH3775c from Dow Corning Toray Co., Ltd. was used as the dimethylsiloxane-methylpolyoxyethylenesiloxane copolymer.
*2Trefil E-508 from Dow Corning Toray Co., Ltd. was used as the spherical organopolysiloxane elastomer powder.

(Method of Preparation)

A: Ingredients 1-7 were heated to 80° C. and uniformly dispersed.

B: Ingredients 8-11 were added to A and uniformly dispersed.

C: Ingredients 12-14 were uniformly mixed.

D: C was added to B at 50° C. and the mixture was emulsified.

E: Upon cooling, ingredient 15 was added and mixed with D, yielding an emulsified foundation (W/O type).

Evaluation of the in-use sensory feel of the emulsified foundation (W/O type) of Practical Example 14 revealed that the emulsified (W/O type) foundation prepared in accordance with this recipe exhibited superior makeup holding properties and wrinkle-hiding effects, a smooth "as-applied" feel, good affinity to the skin and excellent stability.

Practical Example 15

Oil Cleansing Gel (Rinse-Off Type)

| (Composition) | (%) |
|---|---|
| 1. Gelling agent (Synthesis Example 15) | 6.0 |
| 2. Paraffin Wax | 30.0 |
| 3. Decamethylpentasiloxane | 56.0 |
| 4. Polyoxyethylene-methylpolysiloxane copolymer*1 | 5.0 |
| 5. Propylene glycol | 3.0 |

*1SH3772c from Dow Corning Toray Co., Ltd. was used as the dimethylsiloxane-methylpolyoxyethylenesiloxane copolymer.

(Method of Preparation)
Ingredients 1-5 were uniformly mixed at 80° C., producing a cleansing gel.
(Method of Evaluation)
Commercially available skin oil-resistant foundation and long-lasting type lipstick were applied to the skin, after which an appropriate amount of the oil cleansing gel of Practical Example 15 was applied to the coating film, rubbed in with fingers to mix it with the film, washed off with water and then cleaned with soap.
(Evaluation Results)
The foundation and lipstick applied to the skin were completely washed off using the cleansing gel, which showed that the gel had superior cleansing power. In addition, the sensory feel achieved by the gel was the unique light sensory feel characteristic of silicone oils, and its in-use sensory feel was superior as well.

Practical Example 16

Oil Cleansing Gel (Wipe-Off Type)

| (Composition) | (wt %) |
|---|---|
| 1. Gelling agent (Synthesis Example 14) | 6.0 |
| 2. Tri caprylic/capric glyceride ester | 32.0 |
| 3. Decamethylpentasiloxane | 59.0 |
| 4. Propylene glycol | 3.0 |

(Method of Preparation)
Ingredients 1-5 were uniformly mixed at 80° C., producing a cleansing gel.
(Method of Evaluation)
Commercially available skin oil-resistant foundation and long-lasting type lipstick were applied to the skin, after which an appropriate amount of the oil cleansing gel of Practical Example 16 was applied to the coating film, rubbed in with fingers to mix it with the film, and then wiped off with a cotton ball. In addition, a cleansing agent, which had been prepared in the same manner as in Practical Example 16, with the exception of using decamethylpentasiloxane instead of the gelling agent, was subjected to evaluation in the same manner.
(Evaluation Results)
The skin oil resistant oily foundation and lipstick applied to the skin were completely wiped off when the cleansing gel was used, which showed that the gel had superior cleansing power. In addition, the sensory feel produced by the gel was the unique light sensory feel characteristic of silicone oils, its in-use sensory feel was excellent, and the gel also had superior transparency. On the other hand, when the gelling agent was not used, traces of residual skin oil-resistant oily foundation were remained, and the cleansing performance was insufficient. In addition, when the gelling agent of the present invention was not used, the viscosity of the gel was low, causing it to run, and its in-use sensory feel was poor as well.

Practical Example 17

Lipstick

| (Ingredients) | (wt %) |
|---|---|
| 1. Gelling agent (Synthesis Example 13) | 8.0 |
| 2. Glyceryl triisostearate | 20.0 |
| 3. Dimethylpolysiloxane (6 mPa-s) | 5.0 |
| 4. Decamethylpentasiloxane | 30.0 |
| 5. Polyoxyethylene-methylpolysiloxane copolymer*1 | 3.0 |
| 6. Trimethylsiloxysilicic acid | 8.0 |
| 7. Alkyl modified polysiloxane*2 | 3.0 |
| 8. Methylphenylpolysiloxane | 5.0 |
| 9. Silicone-treated pigment | Suitable amount |
| 10. Dye | Suitable amount |
| 11. Synthetic sodium magnesium silicate | 1.0 |
| 12. Fragrance | Suitable amount |

*1SH3775c from Dow Corning Toray Co., Ltd. was used as the dimethylsiloxane-methylpolyoxyethylenesiloxane copolymer.
*2DC2503 from Dow Corning Toray Co., Ltd. was used as the alkyl modified polysiloxane.

(Method of Preparation)
A: Ingredients 1-8 were uniformly mixed and stirred under heating at 80° C.
C: Ingredients 9-12 were uniformly dispersed.
C: B was slowly added to A, the mixture was packed into a container, yielding a lipstick.

Evaluation of the in-use sensory feel of the lipstick of Practical Example 17 revealed that the lipstick obtained from the above-described composition had the unique silicone-like light sensory feel and at the same time exhibited a smooth "as applied" feel and transparent appearance.

The invention claimed is:

1. A cosmetic containing:
  a gelling agent comprising an organopolysiloxane having a silicon-bonded organic group (—Y) represented by general formula (1):

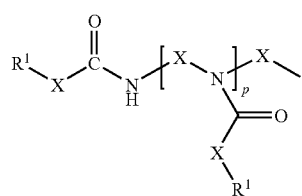

(1)

wherein $R^1$ designates a group containing metal salt of a carboxylic acid represented by formula —COO$^-$ ($M^{n+}$)$_{1/n}$ (where M is a metal that has a valence of 1 or higher, and n is the valence of M); X's designate the same or different $C_2$ to $C_{14}$ bivalent hydrocarbon groups; and p designates an integer from 0 to 10, and a silicone oil, wherein a portion or all of the silicone oil is constituted by any one of linear organopolysiloxanes shown by the following general formula (10), cyclic organopolysiloxanes shown by the general formula (11), or branched organopolysiloxanes shown by the general formula (12)

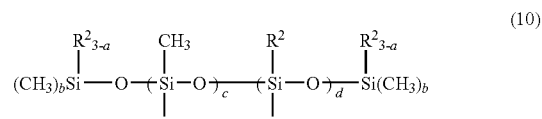

(10)

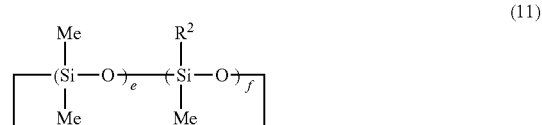

(11)

(12)

in general formulae (10) to (12), $R^2$ is a group selected from $C_{2-30}$ monovalent fluorine-substituted alkyl groups, amino-substituted alkyl groups, and groups represented by $(CH_3)_3SiO\{(CH_3)_2SiO\}_hSi(CH_3)_2CH_2CH_2$, the subscript c is an integer of 0 to 1000, d is an integer of 0 to 1000, c+d is an integer of 1 to 2000, a is 0, 1, or 2, b is 0, 1 or 2, e is an integer of 0 to 8, f is an integer of 1 to 8, such that $3 \leq e+f \leq 8$, g is an integer of 1 to 3, and h is an integer of 0 to 500.

2. A cosmetic containing:
  a gelling agent comprising an organopolysiloxane having a silicon-bonded organic group (—Y) represented by general formula (1) and an optionally substituted $C_9$ or more univalent hydrocarbon group (—Z):

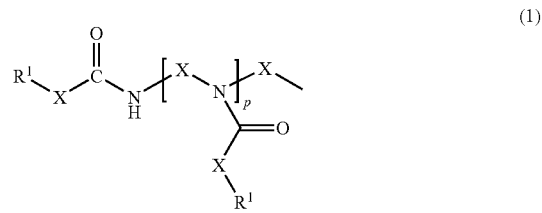

(1)

wherein $R^1$ designates a group containing metal salt of a carboxylic acid represented by formula —COO$^-$ ($M^{n+}$)$_{1/n}$ (where M is a metal that has a valence of 1 or higher, and n is the valence of M); X's designate the same or different $C_2$ to $C_{14}$ bivalent hydrocarbon groups; and p designates an integer from 0 to 10, and a silicone oil, wherein a portion or all of the silicone oil is constituted by any one of linear organopolysiloxanes shown by the following general formula (10), cyclic organopolysiloxanes shown by the general formula (11), or branched organopolysiloxanes shown by the general formula (12)

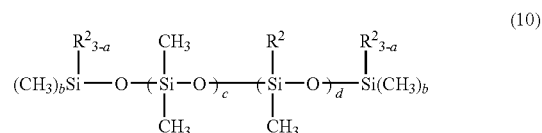

(10)

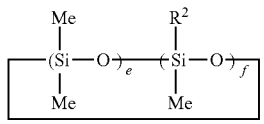

(11)

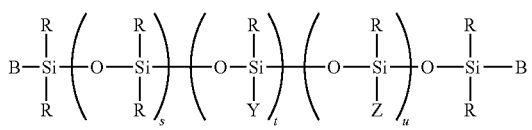

(12)

in general formulae (10) to (12), $R^2$ is a group selected from $C_{2-30}$ monovalent fluorine-substituted alkyl groups, amino-substituted alkyl groups, and groups represented by $(CH_3)_3SiO\{(CH_3)_2SiO\}_h Si(CH_3)_2 CH_2 CH_2$, the subscript c is an integer of 0 to 1000, d is an integer of 0 to 1000, c+d is an integer of 1 to 2000, a is 0, 1, or 2, b is 0, 1 or 2, e is an integer of 0 to 8, f is an integer of 1 to 8, such that $3 \leqq e+f \leqq 8$, g is an integer of 1 to 3, and h is an integer of 0 to 500.

3. The cosmetic according to claim 1, wherein the gelling agent is a linear-chain organopolysiloxane represented by general formula (2):

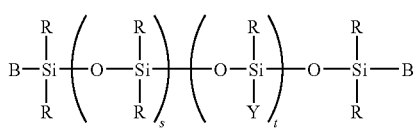

(2)

wherein R designates an optionally substituted $C_1$ to $C_8$ univalent hydrocarbon group {except for the organic group represented by general formula (1)}, Y designates an organic group of general formula (1), B is R or Y, the subscript "s" designates an integer in the range of 10 to 100,000, and "t" designates an integer between 0 and 50, and wherein when t=0, at least one of the two B's is Y.

4. The cosmetic according to claim 2, wherein the gelling agent is a linear-chain organopolysiloxane represented by general formula (3):

(3)

wherein R designates an optionally substituted $C_1$ to $C_8$ univalent hydrocarbon group, {except for the organic group represented by general formula (1)}, Y designates an organic group of general formula (1), Z designates an aforementioned optionally substituted $C_9$ or more univalent hydrocarbon group {except for the organic group represented by general formula (1)}, B is R, Y or Z, the subscript "s" designates an integer in the range of 10 to 100,000, "t" designates an integer between 0 and 50, and "u" designates an integer between 0 and 1000, and wherein when t=0, at least one of the two B's is Y, when u=0, at least one of the two B's is Z, and when t=0 and u=0, one of the two B's is Y and another is Z.

5. A cosmetic containing a gelatinous composition comprising:
(a) 1 to 99 wt. % of gelling agent comprising an organopolysiloxane having a silicon-bonded organic group (—Y) represented by general formula (1) of claim 1; and
(b) 99 to 1 wt. % of the silicone oil of claim 1.

6. A cosmetic containing a gelatinous composition comprising:
(a) 1 to 99 wt. % of gelling agent comprising an organopolysiloxane having a silicon-bonded organic group (—Y) represented by general formula (1) of claim 2 and an optionally substituted $C_9$ or more univalent hydrocarbon group (—Z); and
(b) 99 to 1 wt. % of the silicone oil of claim 2.

7. The cosmetic according to claim 1, wherein, in the general formula (1), M is an alkali metal and the divalent hydrocarbon groups X are alkylene groups.

8. The cosmetic according to claim 5, wherein the silicone oil is a volatile silicone oil.

9. The cosmetic according to claim 5, wherein the silicone oil is a hydrophobic silicone oil which viscosity at 25° C. is in the range of from 0.65 to 100,000 mm$^2$/s.

10. The cosmetic according to claim 5, wherein the index of refraction of the gelatinous composition is in the range of from 1.20 to 1.60.

11. The cosmetic according to claim 1, further comprising (c) one, two, or more ingredients selected from the group comprising anionic surfactants, cationic surfactants, nonionic surfactants, amphoteric surfactants, and zwitterionic surfactants.

12. The cosmetic according to any of claim 1, further comprising (d) a powder and/or a colorant.

13. The cosmetic according to claim 12, wherein ingredient (d) is one, two, or more powders and/or colorants selected from the group comprising resin powders, organic pigment powders, and inorganic pigment powders whose mean particle size is in the range of from 1 nm to 20 μm.

14. The cosmetic according to claim 1, further comprising (e) a water-soluble polymer.

15. The cosmetic according to claim 1, further comprising (f) a silicone resin.

16. The cosmetic according to claim 1, further comprising (g) a silicone elastomer.

17. The cosmetic according to claim 1, further comprising (h) a UV-ray protective component.

18. A personal care product comprising the cosmetic according to claim 1.

19. A skin cleansing product comprising the cosmetic according to claim 1.

20. The cosmetic according to claim 5, wherein component (b) further comprises a non-polar organic compound, a low-polar organic compound, or mixtures thereof.

21. The cosmetic according to claim 5, wherein component (b) further comprises a non-polar organic compound, a low-polar organic compound, or mixtures thereof.

* * * * *